(12) United States Patent
Ackermann et al.

(10) Patent No.: US 10,337,048 B2
(45) Date of Patent: Jul. 2, 2019

(54) METHODS FOR UNIVERSAL DETERMINATION OF ANTICOAGULANT ACTIVITY

(71) Applicant: Roche Diagnostics Operations, Inc., Indianapolis, IN (US)

(72) Inventors: Friedrich Ackermann, Heidelberg (DE); Andreas Calatzis, Munich (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 14/966,296

(22) Filed: Dec. 11, 2015

(65) Prior Publication Data

US 2016/0326568 A1 Nov. 10, 2016

Related U.S. Application Data

(63) Continuation of application No. PCT/EP2014/063520, filed on Jun. 26, 2014.

(30) Foreign Application Priority Data

Jun. 28, 2013 (EP) .................................. 13174242

(51) Int. Cl.
  *G01N 33/86* (2006.01)
  *C12Q 1/56* (2006.01)

(52) U.S. Cl.
  CPC ........ *C12Q 1/56* (2013.01); *C12Y 304/21006* (2013.01); *G01N 33/86* (2013.01); *G01N 2333/96444* (2013.01); *G01N 2496/00* (2013.01); *G01N 2500/20* (2013.01)

(58) Field of Classification Search
  None
  See application file for complete search history.

(56) References Cited

U.S. PATENT DOCUMENTS

| | | | |
|---|---|---|---|
| 4,139,415 A * | 2/1979 | Yin .................. | G01N 33/86 435/13 |
| 6,207,399 B1 * | 3/2001 | Hemker ............. | C07K 5/06026 435/13 |
| 8,932,826 B2 | 1/2015 | Zander | |
| 9,133,501 B2 * | 9/2015 | Harenberg .............. | C12Q 1/56 |
| 2007/0037236 A1 | 2/2007 | Klein et al. | |
| 2016/0015793 A1 * | 1/2016 | Hollenbach ........ | A61K 38/4846 514/13.7 |

FOREIGN PATENT DOCUMENTS

| | | |
|---|---|---|
| EP | 1734369 A1 | 12/2006 |
| EP | 2348319 A1 | 7/2011 |
| GB | 2485590 A | 5/2012 |
| WO | 2001/007070 A1 | 2/2001 |
| WO | 2008/052718 A1 | 5/2008 |
| WO | 2010/121196 A1 | 10/2010 |
| WO | 2012/140580 A1 | 10/2012 |

OTHER PUBLICATIONS

Castro-Lopez V. et al. Comparative Study of Factor Xa Fluorogenic Substrates and Their Influence on the Quantification of LMWHs. Analytical and Bioanalytical Chemistry 399(2)691-700, 2011.*
Gehrie E. et al. Test of the Month: The Chromogenic Antifactor Xa Assay. American J Hematology 87(2)194-196, Feb. 2012.*
Calatzis A. et al. Prothrombinase Induced Clotting Time Assay . . . American J of Clinical Pathology 130(3)446-454, Sep. 2008.*
Samama M. et al. Evaluation of the Anti-Factor Xa Chromogenic Assay for the Measurement of Rivaroxaban Plasma Concentrations Using Calibrators and Controls. Thrombosis and Haemostasis 107(2)379-387, Feb. 2012.*
Depasse F. et al. Assessment of Three Chromogenic and One Clotting Assays for the Measurement of Synthetic Pentasaccharide Fondaparinux (Atrixra) Anti-Xa Activity. J of Thrombosis and Haemostasis 2(2)346-348, 2004.*
International Search Report dated Sep. 4, 2014 in Application No. PCT/EP2014/063520, 4 pages.
Favaloro, Emmanuel J. et al., Laboratory testing of anticoagulants: the present and the future, Pathology, 2011, pp. 682-692, vol. 43, No. 7.
Gehrie, Eric and Laposata, Michael, Test of the Month: The chromogenic antifactor Xa assay, American Journal of Hematology, 2012, pp. 194-196, vol. 87.
Needleman, Saul B. and Wunsch, Christian D., A General Method Applicable to the Search for Similarities in the Amino Acid Sequence of Two Proteins, Journal of Molecular Biology, 1970, pp. 443-453, vol. 48.
Pearson, William R. and Lipman, David J., Improved tools for biological sequence comparison, Proceedings of the National Academy of Sciences USA, 1988, pp. 2444-2448, vol. 85.
Smith, Temple F. and Waterman, Michael S., Comparison of Biosequences, Advances in Applied Mathematics, 1981, pp. 482-489, vol. 2.
Tripodi, Armando, The Laboratory and the New Oral Anticoagulants, Clinical Chemistry, 2013, pp. 353-362, vol. 59, No. 2.

* cited by examiner

*Primary Examiner* — Ralph J Gitomer
(74) *Attorney, Agent, or Firm* — Roche Diagnostics Operations, Inc.

(57) ABSTRACT

The present invention concerns diagnostic methods for coagulation testing involving determining anticoagulant activity elicited by a first anticoagulant in a sample comprising measuring a first Factor Xa activity in a body fluid test sample of said subject, measuring a second Factor Xa activity in at least one calibrator sample comprising a predefined anticoagulation activity for a second anticoagulant, calculating an universal parameter for the anticoagulation activity comprised in the test sample based on the first and the second measured Factor Xa activities and comparing the said parameter for the anticoagulation activity with predefined ranges of expected anticoagulation activity for at least three anticoagulants. Further provided is a computer program code assisting the method as well as a system for carrying out the said method as well as a kit.

9 Claims, 20 Drawing Sheets

_US 10,337,048 B2_

METHODS FOR UNIVERSAL DETERMINATION OF ANTICOAGULANT ACTIVITY

CROSS-REFERENCE TO RELATED APPLICATIONS

This application is a continuation of International Patent Application No. PCT/EP2014/063520 filed Jun. 26, 2014, which claims priority to European Application No. EP13174242.1 filed Jun. 28, 2013, the disclosures of which are hereby incorporated by reference in their entirety.

BACKGROUND OF THE DISCLOSURE

The present invention concerns diagnostic means and methods in the field of coagulation testing. In particular, it relates to a method for determining an anticoagulant activity elicited by a first anticoagulant in a sample of a subject comprising measuring a first Factor Xa activity in a body fluid test sample of said subject, measuring a second Factor Xa activity in at least one calibrator sample comprising a predefined anticoagulation activity for a second anticoagulant, calculating a universal parameter for the anticoagulation activity comprised in the test sample based on the first and the second measured Factor Xa activities and comparing the said parameter for the anticoagulation activity with predefined ranges of expected anticoagulation activity for at least three anticoagulants. Further provided is a computer program code assisting the method as well as a system for carrying out the said method as well as a kit.

Any bigger organism has a blood circulation system, which brings oxygen and nutrients to the different organs, and disposes carbon dioxide and wastes. However for the blood circulation system to function, injuries in the blood vessels have to be closed rapidly and effectively. This function is fulfilled by the blood coagulation system, which is a complex mechanism which allows the blood to form platelet aggregates and fibrin gels, which are able to close vascular injuries.

However, blood clotting can not only lead to hemostasis, i.e. the closing of injuries in blood vessels, but also to thrombosis and embolism, i.e. the closure of blood vessels by blood clots. Thrombosis and embolism can have many manifestations, such as venous thrombosis in the legs, pulmonary embolism, myocardial infarction and stroke. The blood clotting system is therefore an important life-saving process, which can however also cause severe complications and even the death of the patient, if blood clotting closes vital blood vessels.

One mechanism involved in the blood coagulation system is the clotting factor cascade, which is a series of serine proteases, which become serially activated and ultimately lead to the formation of thrombin, the central enzyme of the blood clotting system. Thrombin is able to split fibrinogen to fibrin, which falls out, polymerizes into fibrin fibers, which form a fibrin clot. Thrombin is also activating co-factors, which accelerate its own generation (Factor V and Factor VIII), activates Factor XIII, a transglutaminase, which cross-links and thus stabilizes the fibrin clot, and thrombin is also a potent activator of the blood platelets.

As individuals become older and also accelerated by risk factors such as diabetes, obesity, smoking and genetic risk factors, there is an increasing risk for thrombotic events. Therefore drugs that inhibit the coagulation system have been developed, the so-called anticoagulants. One of the most successful classes of anticoagulant drugs are the inhibitors of Factor Xa, a serine protease which activates prothrombin to thrombin. The formation of Factor Xa is the step directly preceding the activation of thrombin.

Factor Xa is inhibited by several different drugs, such as low molecular weight heparin, Pentasaccharide, Rivaroxaban, Apixaban, and unfractionated heparin. These drugs have different structures, molecular weights, as well as mechanisms, but they share the common feature that they all lead to the inhibition of Factor Xa and therefore to a reduction in thrombin generation.

Most drugs directed against Factor Xa are generally very safe and do not require a routine monitoring of their effect in the clinical application. Still there are situations where the ability to measure the activity of these drugs is desirable: For example when the treating physician suspects that the patient might not reliably take his medication and wants to control the drug level, or if the patient has a disease that might lead to an accumulation of the drug in the circulation and therefore to bleeding complications, or in patients that are very old, in children or severely obese patients, or in patients experiencing complications during their anticoagulant therapy, i.e. bleeding or thrombosis, and the physicians want to elucidate the current anticoagulation status.

Two global assays are commonly used to measure the activity of the clotting factors: The prothrombin time (PT) and the activated partial thromboplastin time (aPTT). In both assays the clotting cascade is stimulated at its beginning (by tissue factor in the PT and by a contact activator in the aPTT) and following a series of enzymatic reactions thrombin is formed and the sample clots. The time between the start of the test and the clotting of the sample is the clotting time which is indicative of the activity of the clotting factors. However in both assays the formation of Factor Xa is only one step out of many and therefore the aPTT and PT have a low sensitivity for most inhibitors of Factor Xa and a poor quantification of the actual drug activity (see, e.g., EP 1 734 369 A1).

More specific methods for quantifying Factor Xa inhibition have been developed. Assays for measuring Factor Xa inhibition are also called "anti-Xa-tests" or "anti-Factor Xa-tests". A common feature of such anti-Factor Xa-tests is that a sample is added to two reagents: One that contains Factor Xa and one that contains a peptide substrate which can be split by Factor Xa. Then the conversion of the peptide substrate by Factor Xa is recorded in the reaction solution. The peptide substrate comprises a certain amino acid sequence which allows it to be cleaved by Factor Xa, whereby the velocity of the conversion is proportional to the activity of Factor Xa in the sample. When the substrate is split by Factor Xa a signal reaction is mediated, which is measured by the analyzer, which performs the anti-Xa test. Usually a chemical group providing a detectable label (such as e.g. a chromogen or a fluorophor) is covalently bound to the peptide substrate. When such chromogenic peptide substrate is used a group which changes the colour of the solution is released, which can be measured photometrically. When a fluorogenic substrate is used a fluorescent group is released and when the reaction is measured electrochemically, the splitting of the substrate by Factor Xa results in the change of the ional structure of the reaction solution. The common feature of the different substrates is that in every case a signal reaction occurs in the sample, which is proportional to the concentration of Factor Xa in the sample and which is recorded by the analyzer.

Between the addition of the reagent containing Factor Xa to the sample and the addition of the reagent containing the substrate there can be an incubation step, in order to allow the Factor Xa inhibitor in the sample to inhibit Factor Xa. However, there are also assays with no such incubation step. Optionally, also other substances can be added which influence the specificity of the assay, such as dextrane sulfate or antithrombin.

The result of the assay is then the change of absorbance, or the rate of change of absorbance, (or fluorescence or any other signal reaction used). For simplicity it is assumed that the signal reaction is the change in absorbance expressed in mE (milli units of extinction).

As known in the art usually, using this absorbance the anticoagulant concentration was calculated using a calibration curve. This procedure was developed when only 2 classes of inhibitors to Factor Xa were therapeutically applied, namely unfractionated heparin (UFH) and low molecular weight heparin (LMWH). Typically, a separate calibration curve was performed with calibrators, which contain increasing doses of LMWH or UFH, and following the measurement of these calibrators the analyzer determines the calibration curve to calculate the anticoagulant concentration from the absorbance values determined with the plasma samples.

In the meantime, several additional Factor Xa inhibitors have been introduced into the clinical practice and calibrators as well as controls for e.g., Rivaroxaban, pentasaccharide, Danaparoid are available.

In any larger hospital, today, many different anticoagulants are simultaneously used. Some patients may receive LMWH for prophylaxis of deep venous thrombosis (DVT) during hospitalization, others may receive Rivaroxaban for the prophylaxis of stroke caused by atrial fibrillation, other patients receive Pentasaccharide for the prevention of DVT in hip replacement surgery, and intensive care unit (ICU) patients may receive therapy with unfractionated heparin.

The clinical process, typically, is as follows: Assistant personal (e.g., a phlebotomist, a nurse or one of the younger medical practitioners) prepares the blood collection tubes for the blood collection and the fills out the respective order forms that specify which assays have to be performed. The blood is collected and transferred to the laboratory together with the order form. If a test for LMWH, UFH, Rivaroxaban or Apixaban has been ordered an anti-Factor Xa test is performed, and the concentration of the anticoagulant is calculated based on the respective calibration curve. This concentration is then transferred to the treating physicians via the laboratory information system (LIS), which is usually available via intranet, or via a fax, letter or other means of information.

However, this procedure for ordering the assays, calibration, and result expression has several shortcomings. These limitations affect the efficiency of the process, but also impose medical risks.

For example, the need to use several sets of calibrators and controls for a single diagnostic method (the anti-Factor Xa-test) is cumbersome, expensive and adds complexity in the laboratory workup. If one imagines that every laboratory test required several different calibrations, controls, and proficiency testing procedures, one can imagine that this would add a great burden in the effort involved with laboratory analysis and also on the costs of a laboratory.

In addition risks are involved, which can be highlighted by the following example: As mentioned previously the order forms for blood tests are usually filled out not by the treating physicians themselves, but by assistant personnel having a lower medical education level or experience (nurses, phlebotomists, young doctors). If now, inadvertently, assistant personal orders a "LMWH" test, while the patient receives Rivaroxaban, the laboratory will report a LMWH concentration, even though the patient might have never been treated with this drug. This means that the expression of the laboratory result is more specific than the analytical method itself. What is measured is Factor Xa inhibition. However, what is reported is the concentration of a particular drug. In another scenario, one may assume that a physician evaluating a patient's laboratory values would see a drop in the platelet count and at the same time acertain LMWH concentration. The said physician could therefore misinterpret this result as a heparin induced thrombocytopenia. The problem is not only that a wrong order is propagated through the process, but the wrong information at the beginning is up-valued through the chain. If a nurse told the physician that the patient has received LMWH, the physician might double check this information. However if the physician receives a "LMWH concentration" in an official report from his laboratory, with the signature of the responsible laboratory staff on it, he will assume that this information is correct.

Therefore the current diagnostic procedure involves a very early selection of the calibration procedure which will be applied much later in the diagnostic process, wrong selections of the drug to be calibrated with are propagated throughout the entire diagnostic process and up-valued. The diagnostic procedure involving a generic measuring step (i.e. Factor Xa inhibition) and a calibration step (against the respective anticoagulant) is not transparent to the user. The calibration procedure is rigid, i.e. once the result has been reported, it is not possible to change the calibration even if the wrong drug has been selected earlier in the process (Favaloro 2011, Pathology, December; 43(7):682-92; Tripodi 2013, Clin Chem, February; 59(2):353-62; and Gehrie 2012, Am J Hematol., February; 87(2):194-6).

The technical problem underlying the present invention can be seen as the provision of means and methods for complying with the aforementioned needs. The technical problem is solved by the embodiments characterized in the claims and herein below.

BRIEF SUMMARY OF THE DISCLOSURE

The present invention concerns diagnostic means and methods in the field of coagulation testing. In particular, it relates to a method for determining an anticoagulant activity elicited by a first anticoagulant in a sample of a subject comprising measuring a first Factor Xa activity in a body fluid test sample of said subject, measuring a second Factor Xa activity in at least one calibrator sample comprising a predefined anticoagulation activity for a second anticoagulant, calculating an universal parameter for the anticoagulation activity comprised in the test sample based on the first and the second measured Factor Xa activities and comparing the said parameter for the anticoagulation activity with predefined ranges of expected anticoagulation activity for at least three anticoagulants. Further provided is a computer program code assisting the method as well as a system for carrying out the said method as well as a kit.

DETAILED DESCRIPTION OF THE DISCLOSURE

Figure 1:
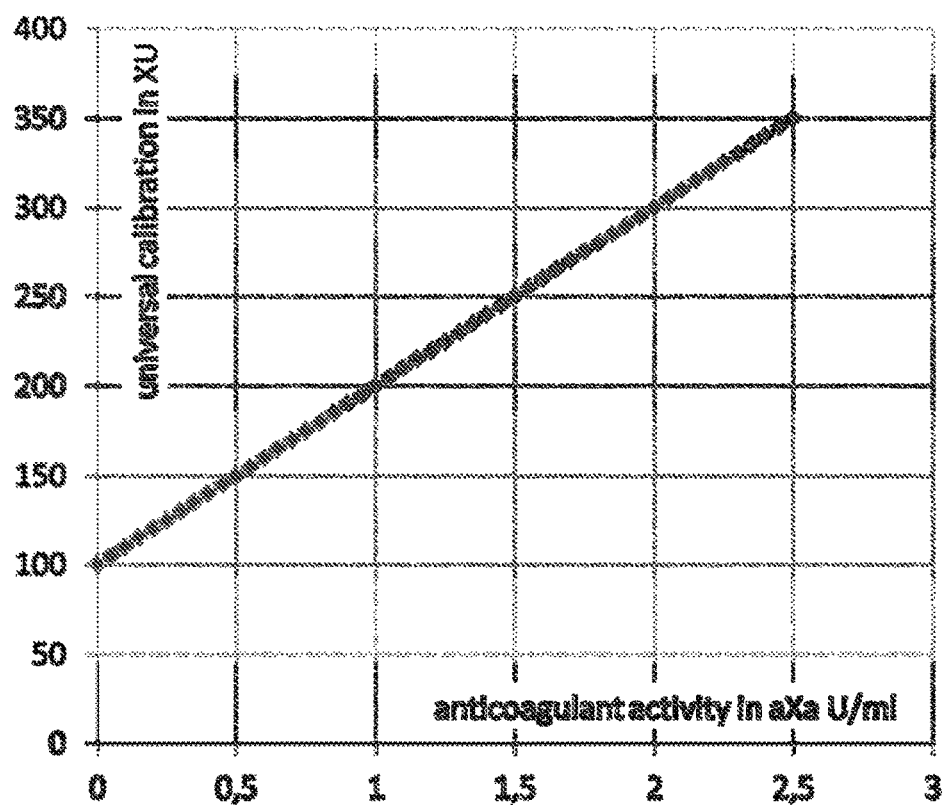
FIG. 1 shows a universal calibration using the LMWH calibrators. Calibration was performed in arbitrary units called "XU" and has been assigned to aXa U/ml (aXa=anti-Factor Xa).
Figure 2A:
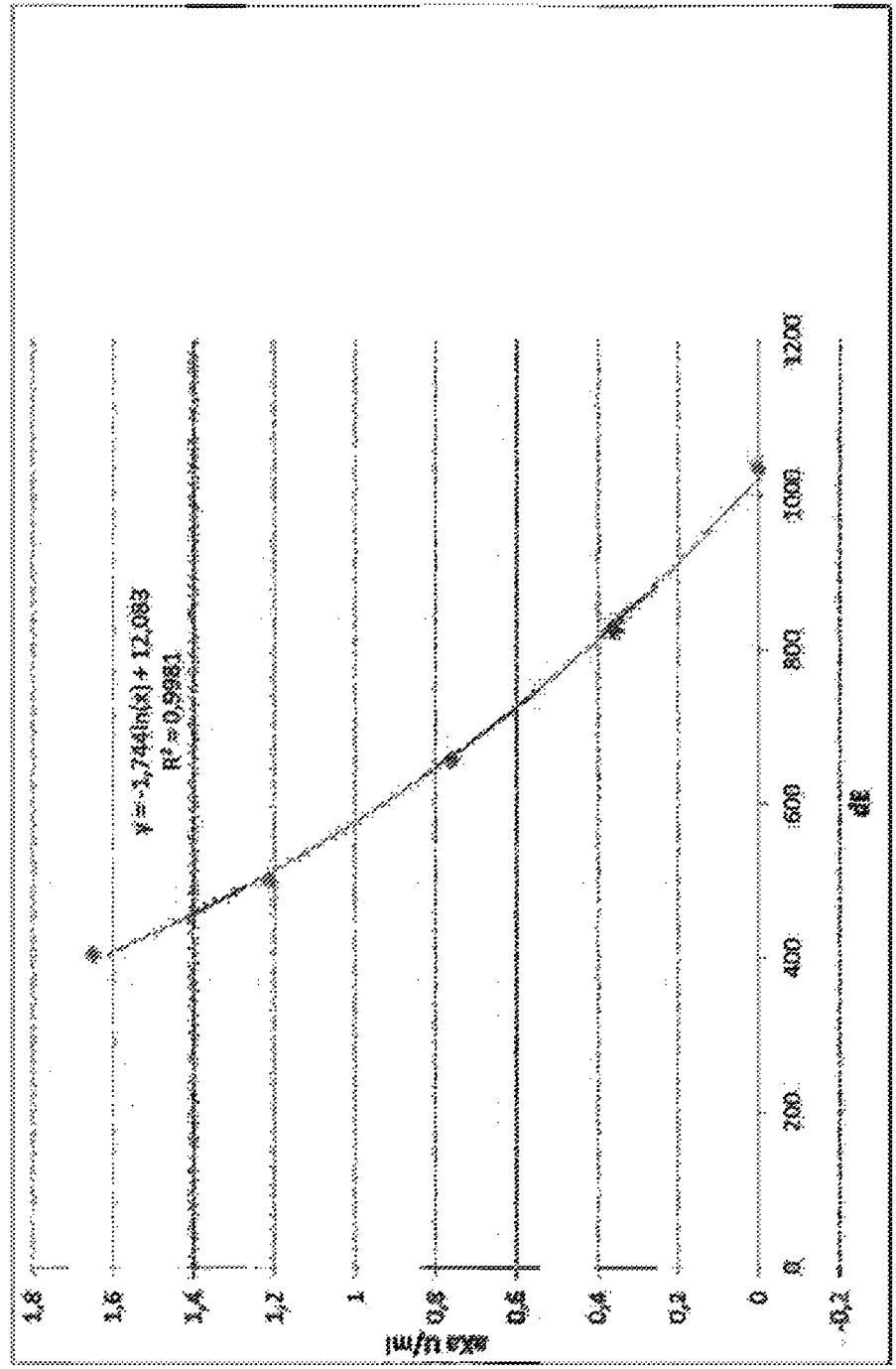
FIG. 2A shows a calibration curve for heparin in Laboratory A.
Figure 2B:
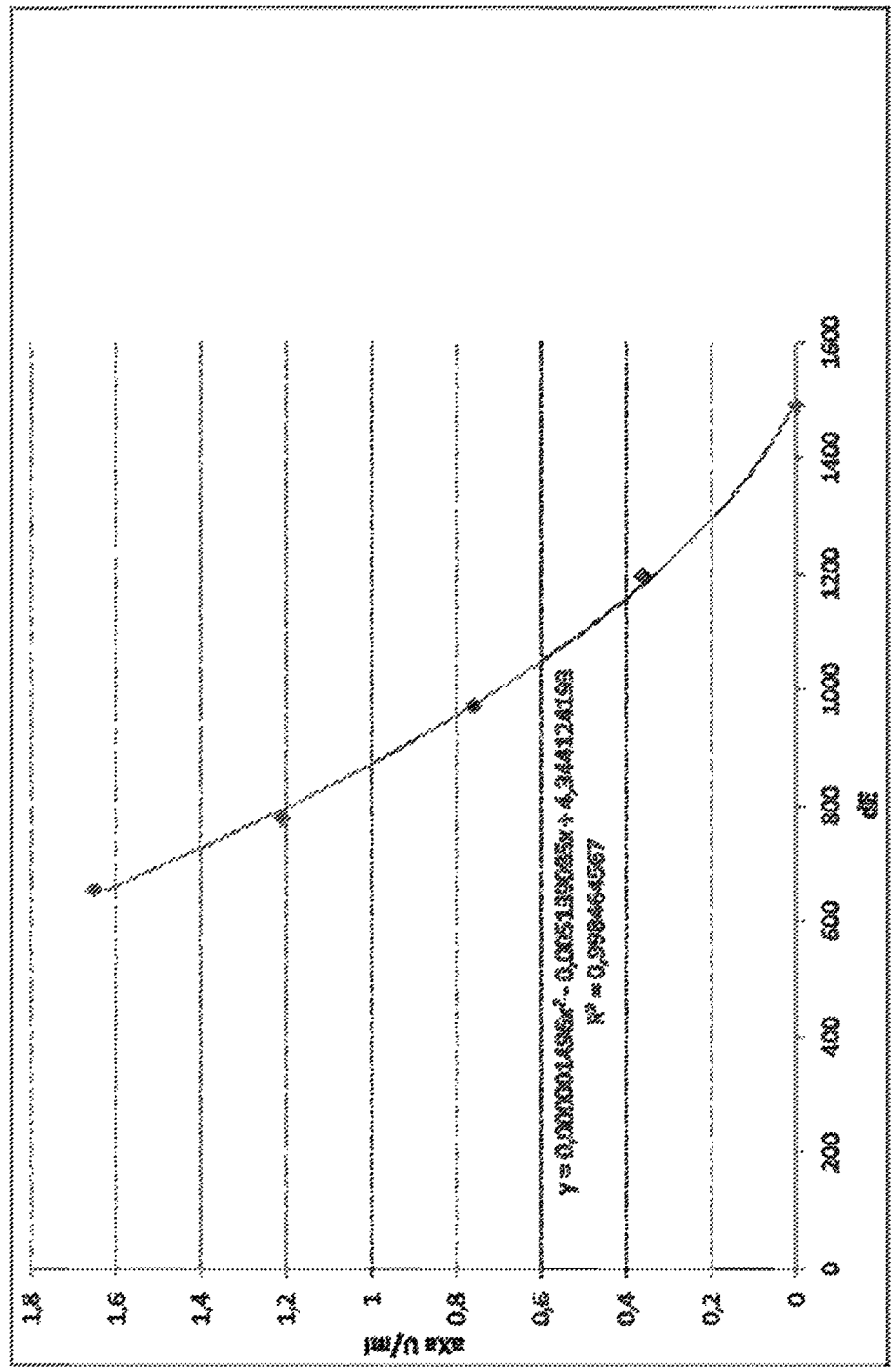
FIG. 2B shows a calibration curve for heparin in Laboratory B.
Figure 2C:
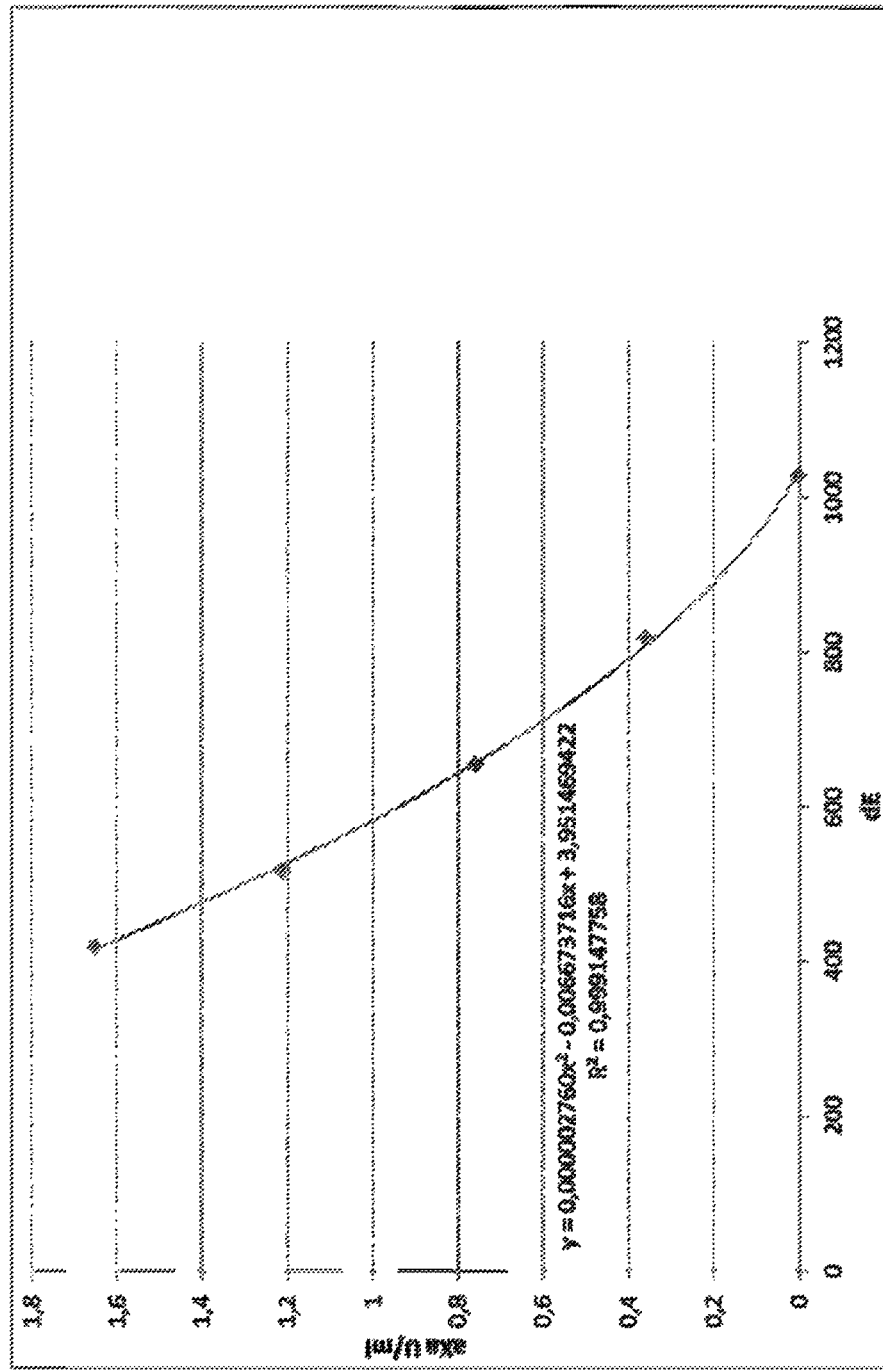
FIG. 2C shows a calibration curve for heparin in Laboratory C.
Figure 2D:
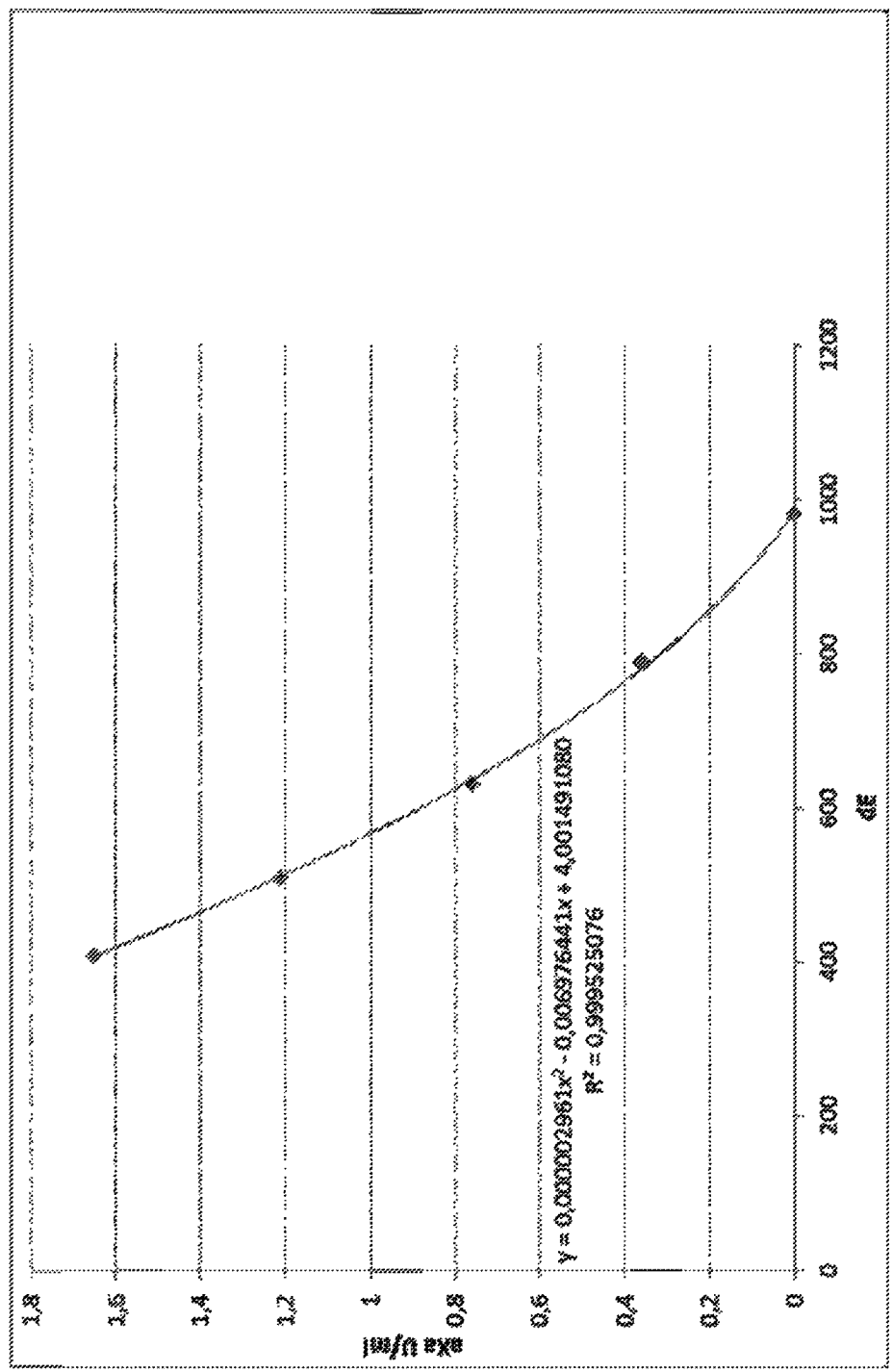
FIG. 2D shows a calibration curve for heparin in Laboratory D.
Figure 3A:
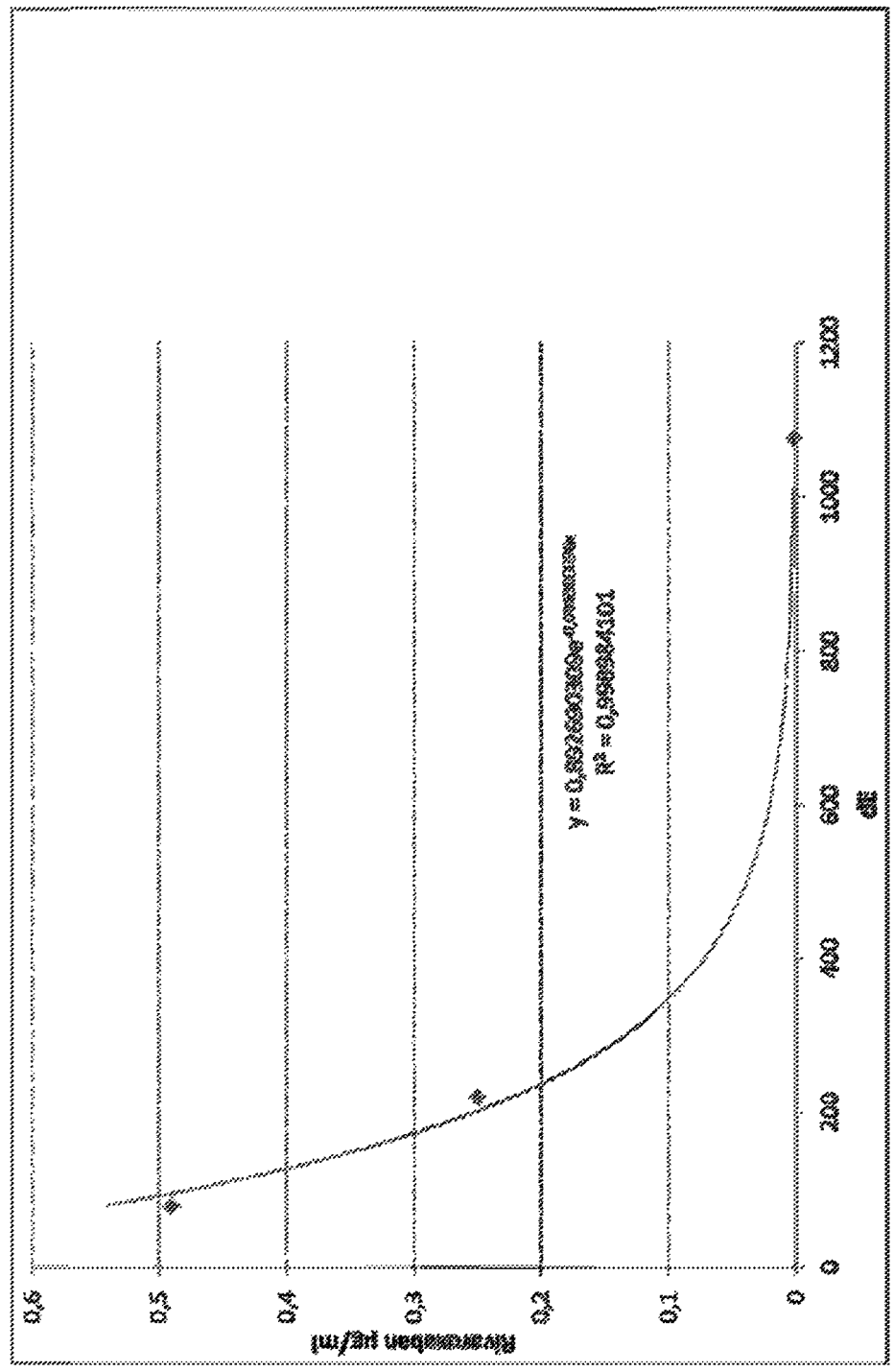
FIG. 3A shows a calibration curve for Rivaroxaban in Laboratory A.
Figure 3B:
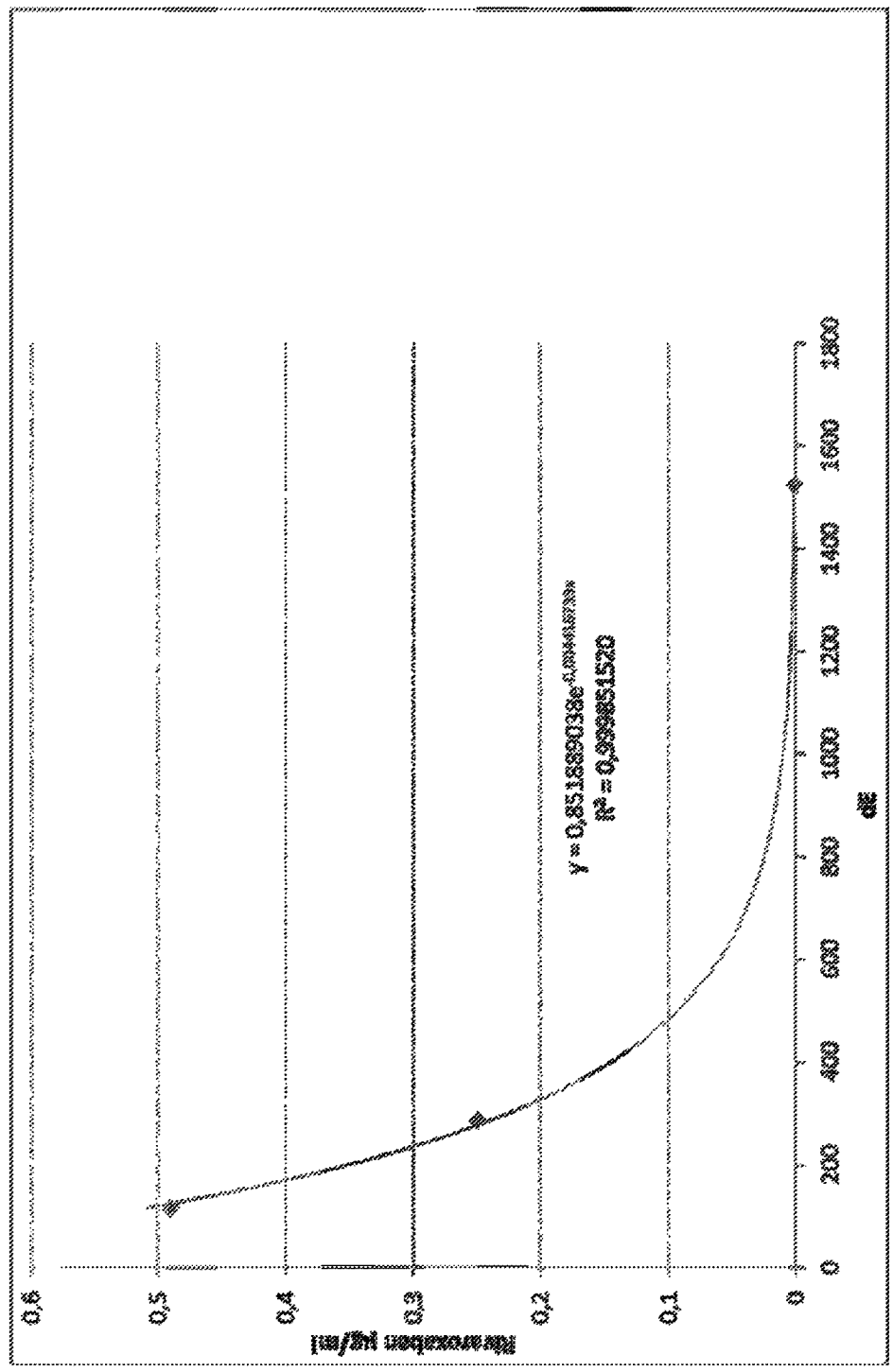
FIG. 3B shows a calibration curve for Rivaroxaban in Laboratory B.
Figure 3C:
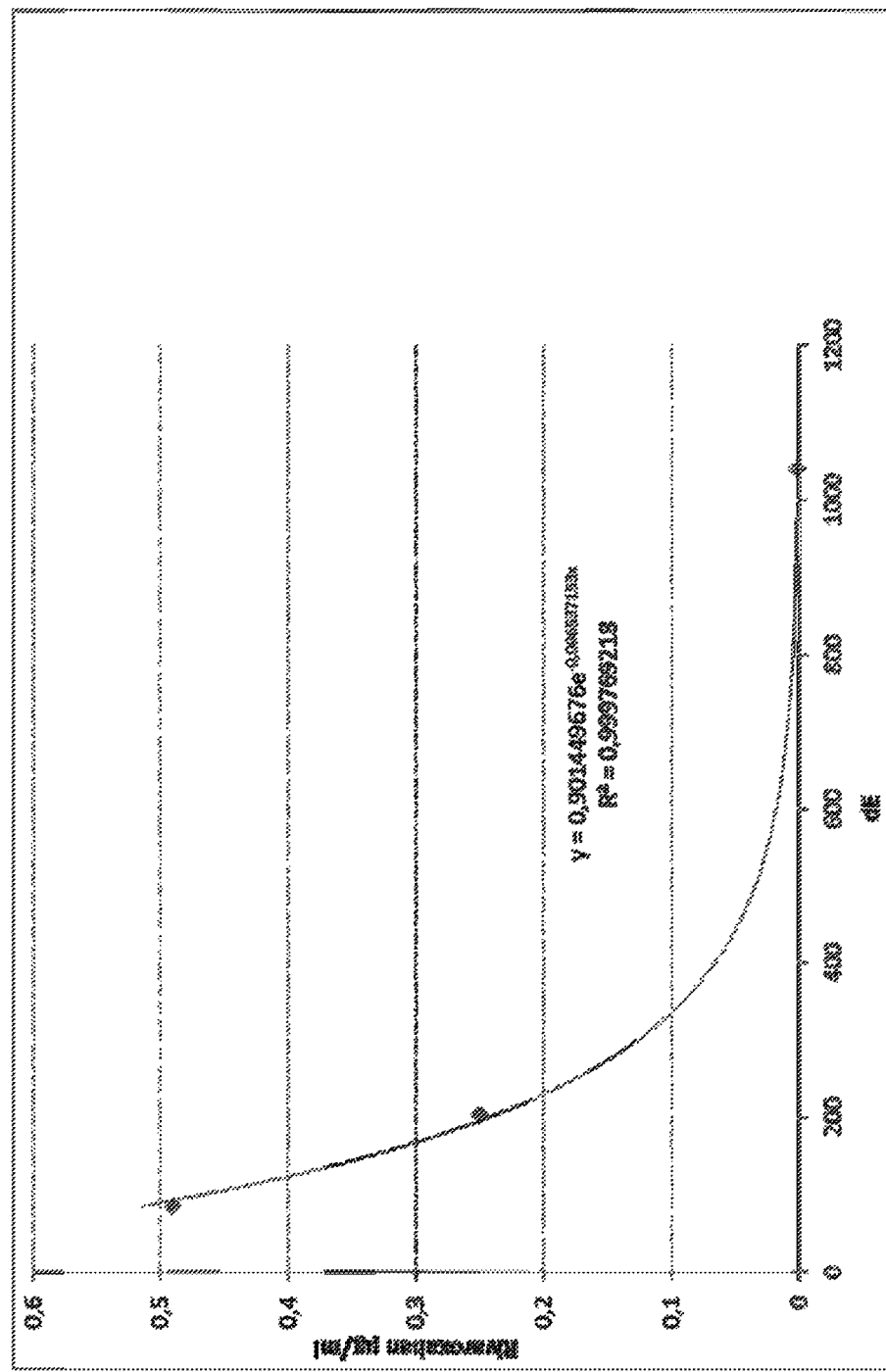
FIG. 3C shows a calibration curve for Rivaroxaban in Laboratory C.
Figure 3D:
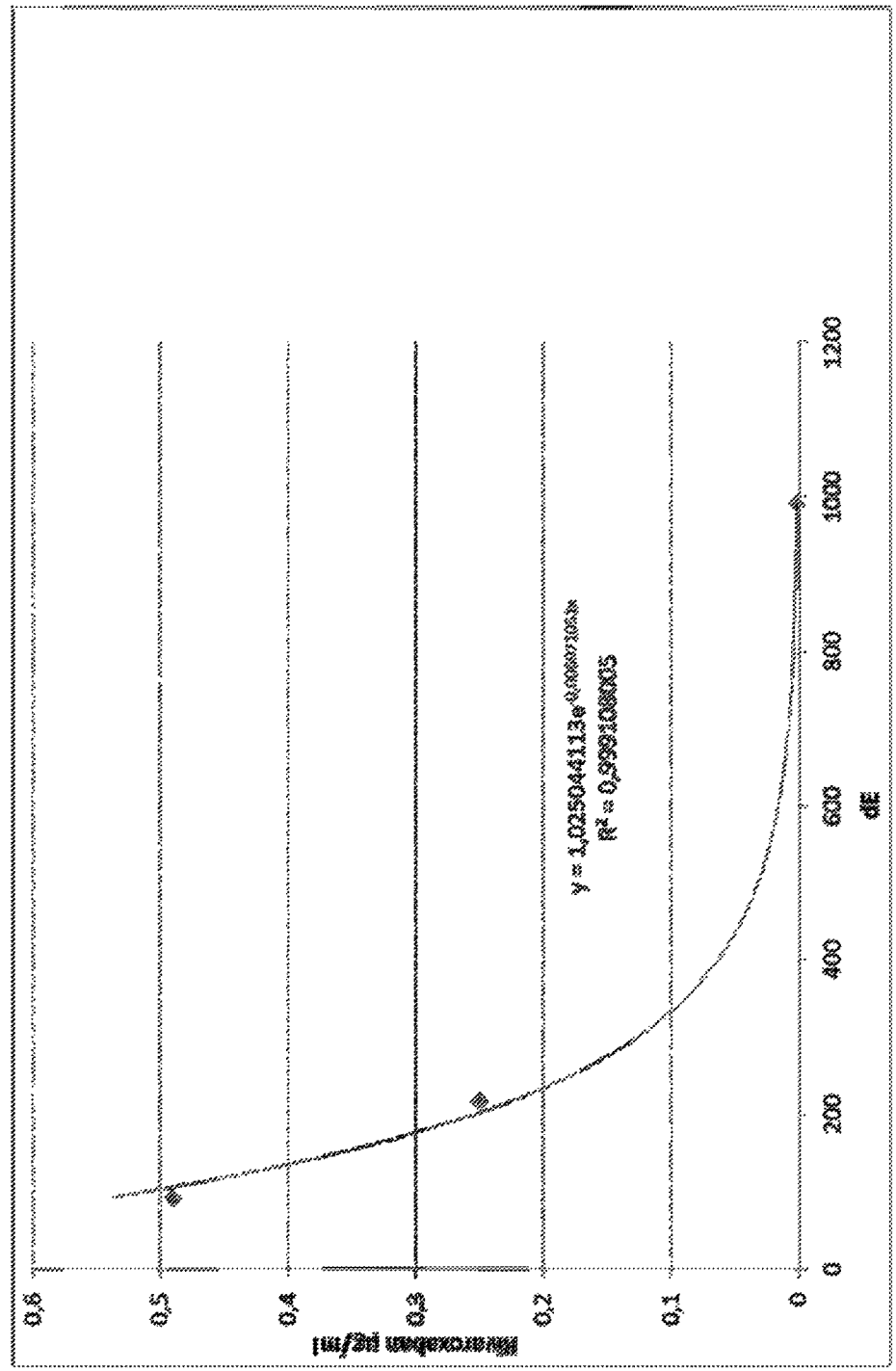
FIG. 3D shows a calibration curve for Rivaroxaban in Laboratory D.
Figure 4A:
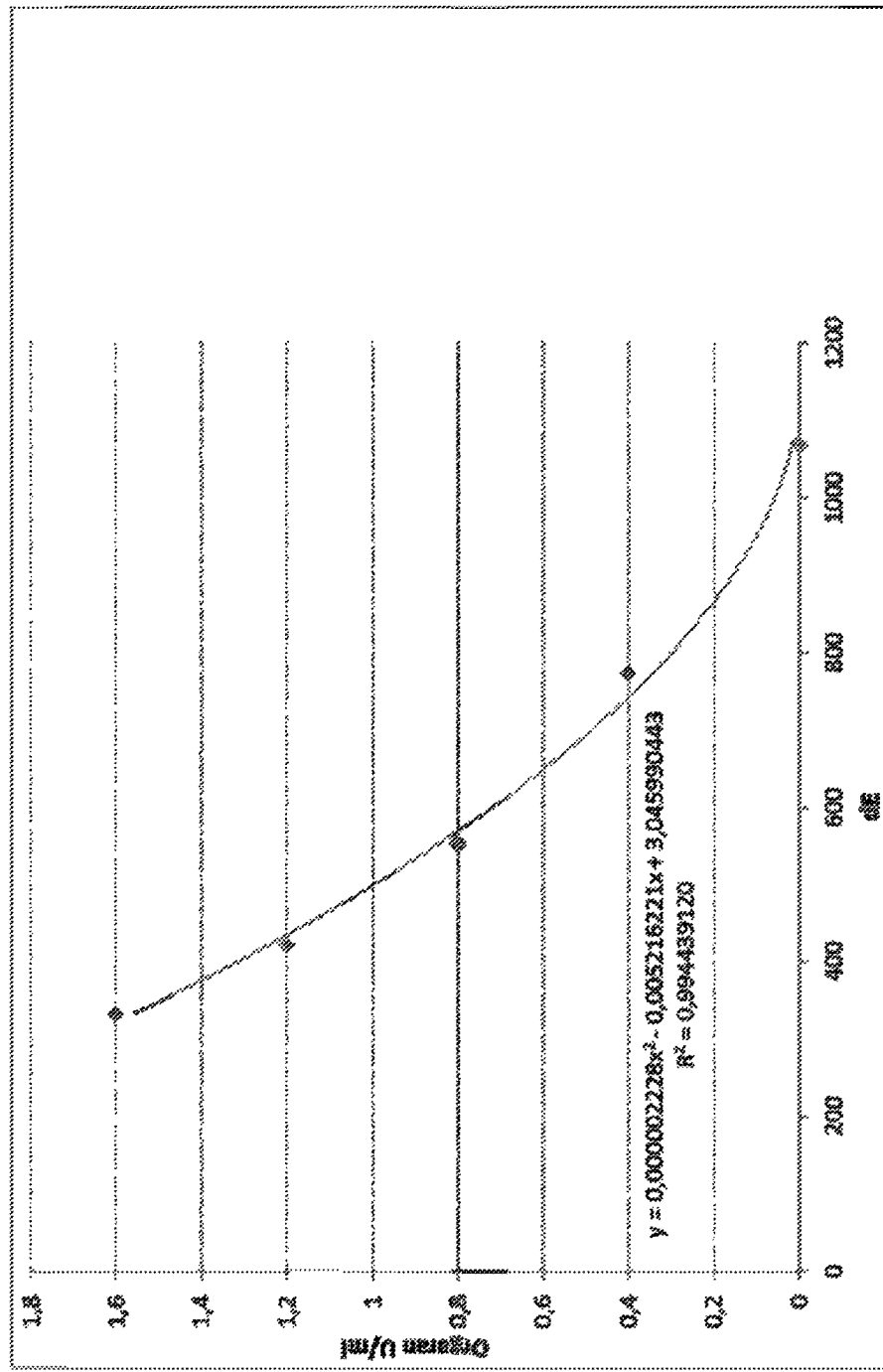
FIG. 4A shows a calibration curve for Organ in Laboratory A.
Figure 4B:
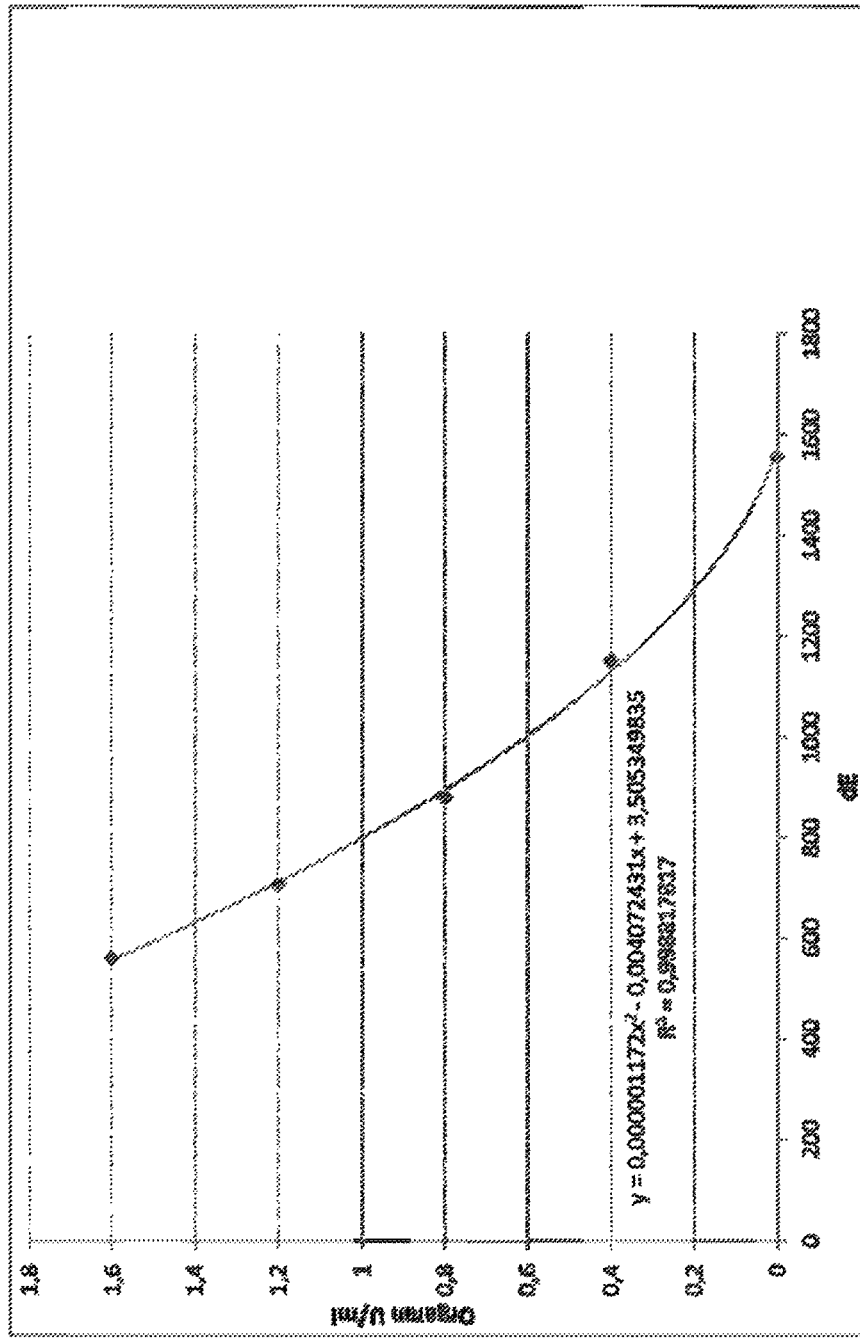
FIG. 4B shows a calibration curve for Organ in Laboratory B.
Figure 4C:
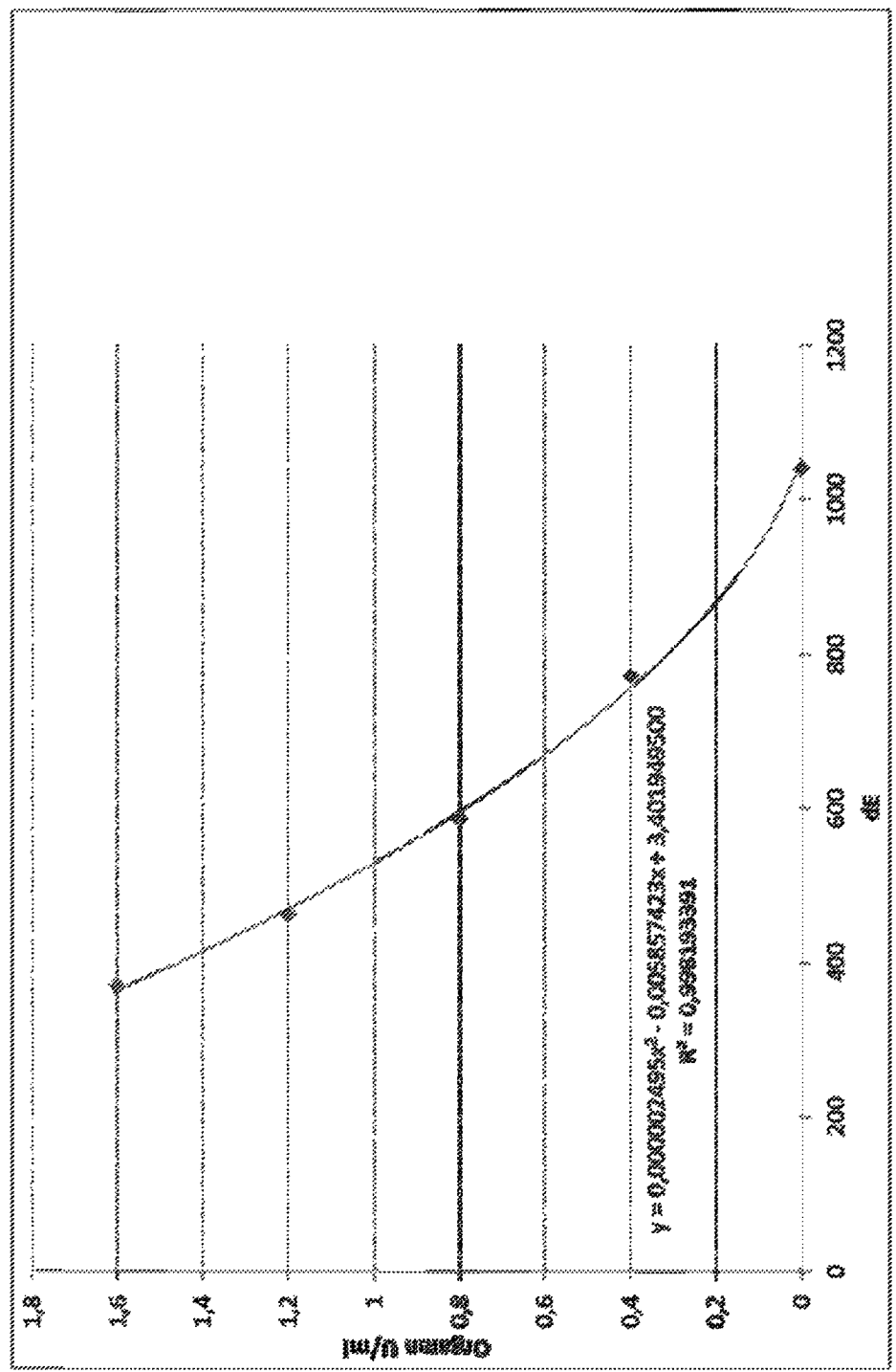
FIG. 4C shows a calibration curve for Organ in Laboratory C.
Figure 4D:
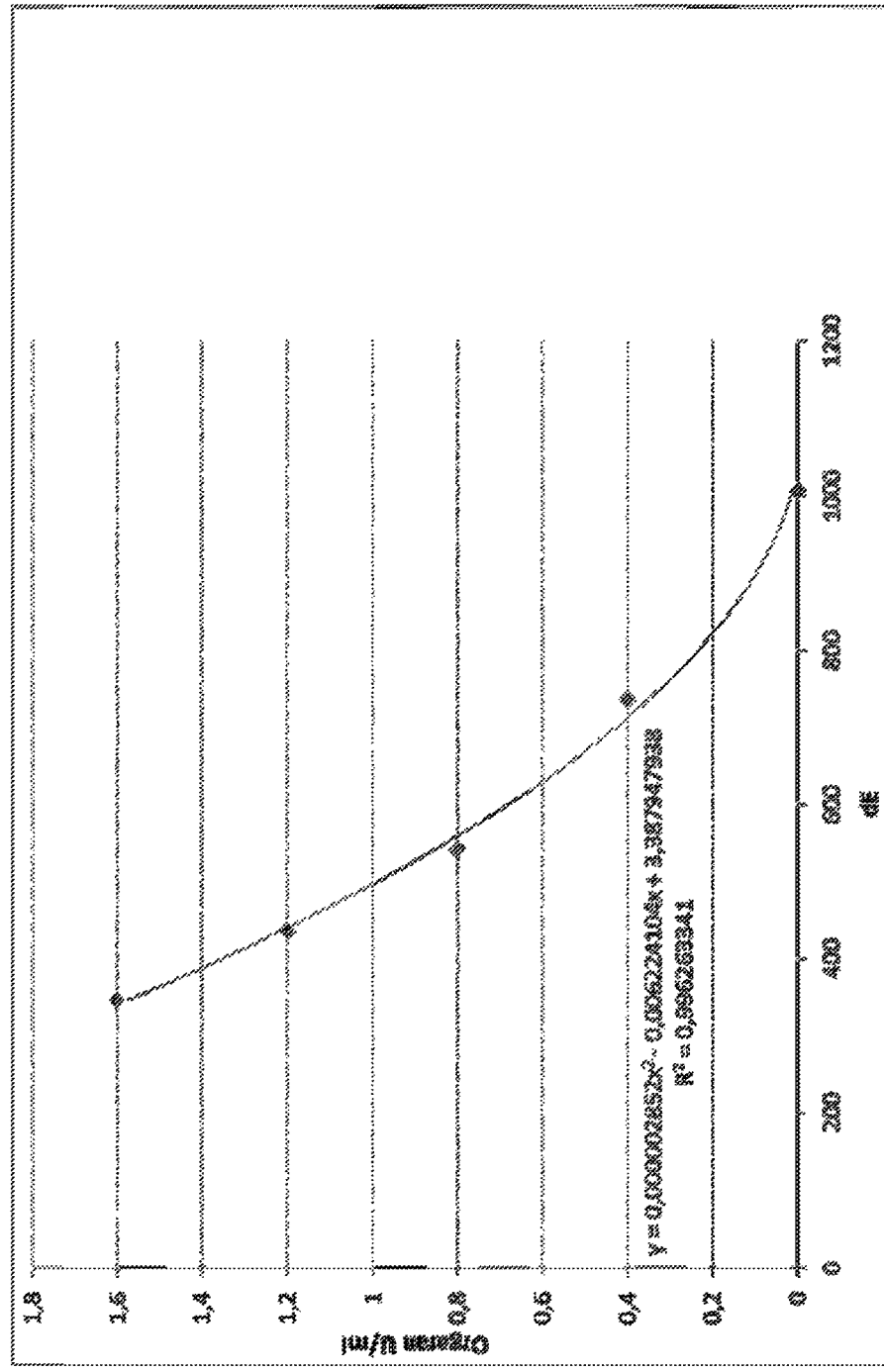
FIG. 4D shows a calibration curve for Organ in Laboratory D.
Figure 5A:
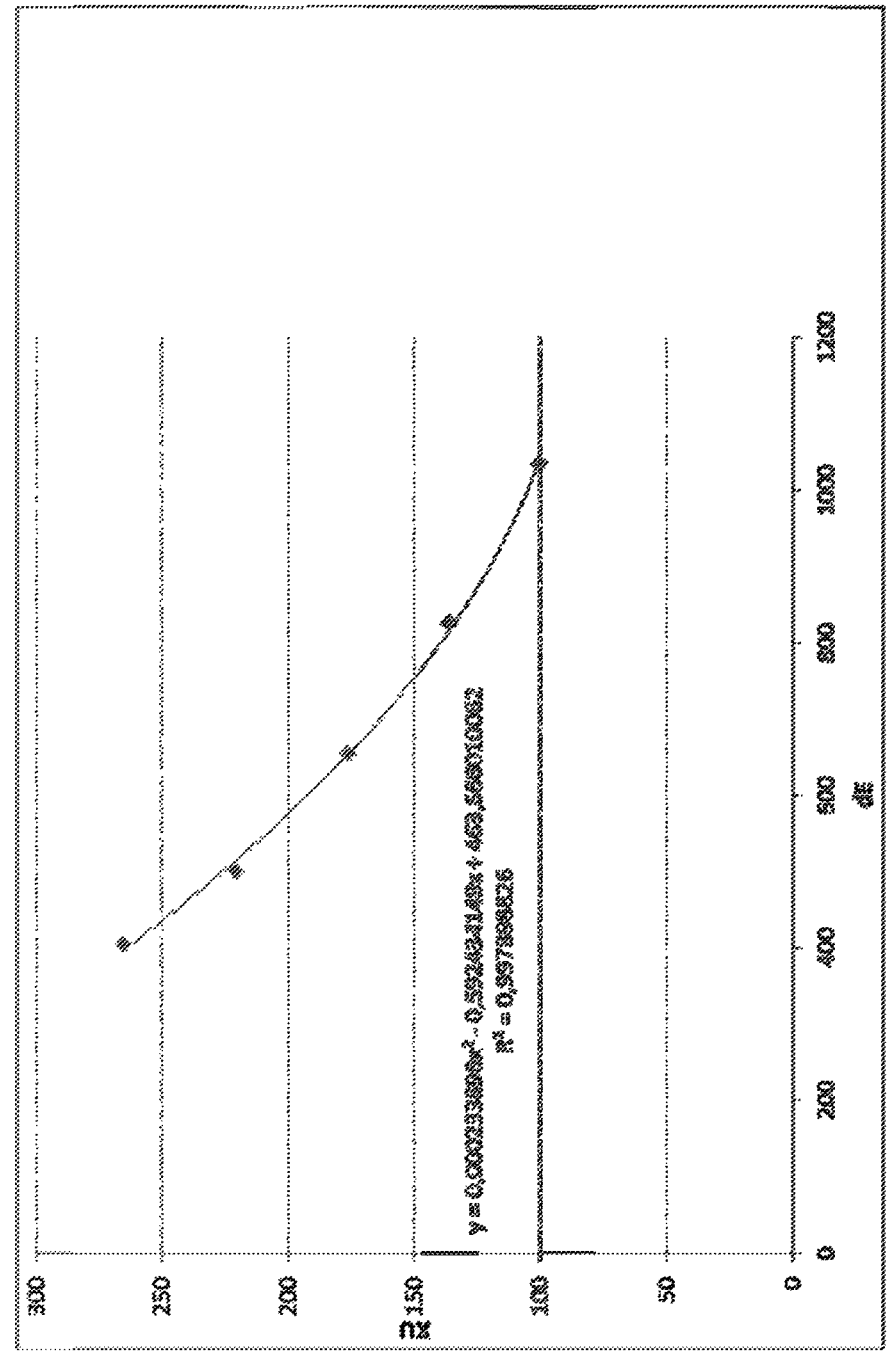
FIG. 5A shows a universal calibration curve in Laboratory A.
Figure 5B:
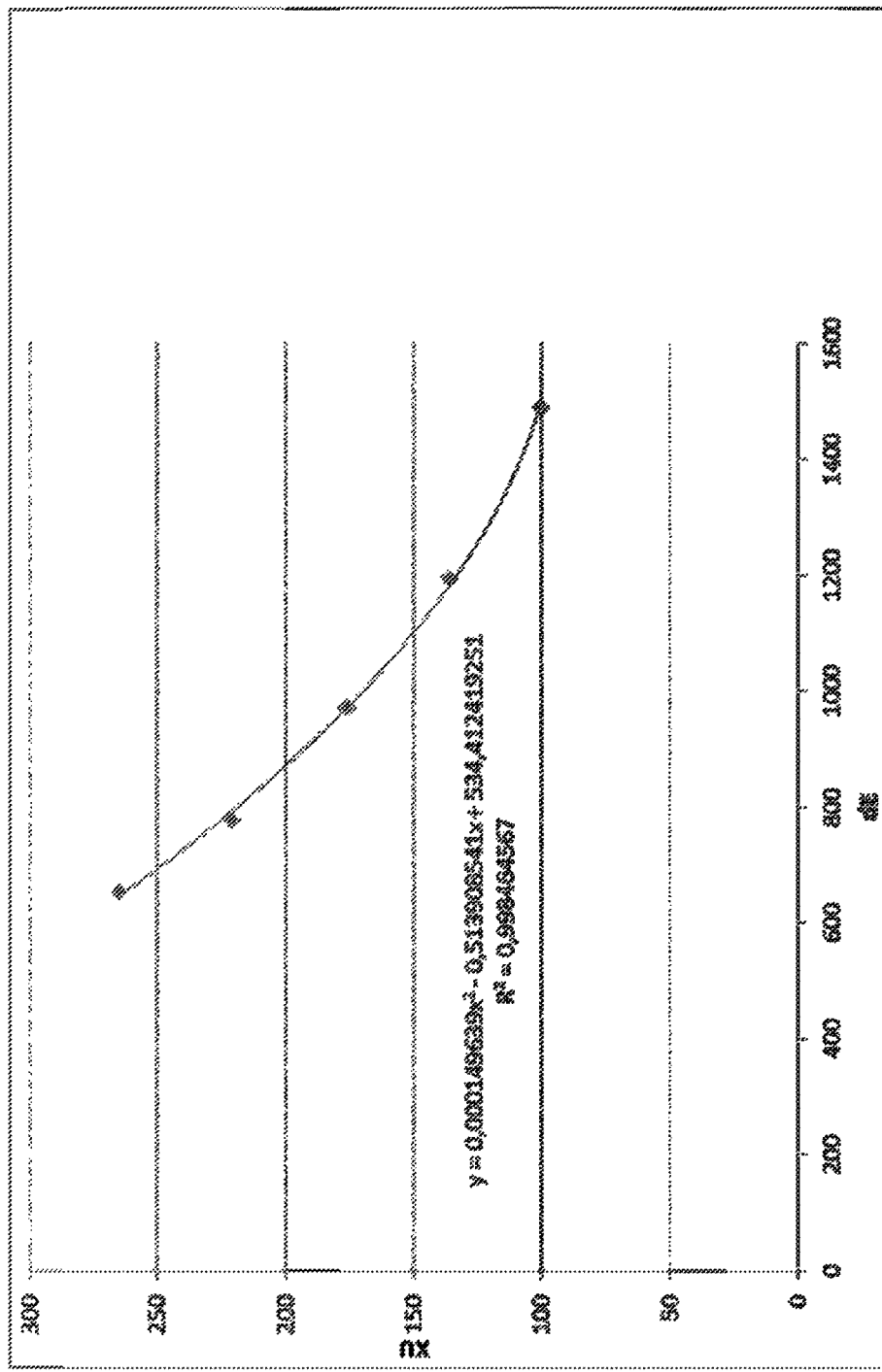
FIG. 5B shows a universal calibration curve in Laboratory B.
Figure 5C:
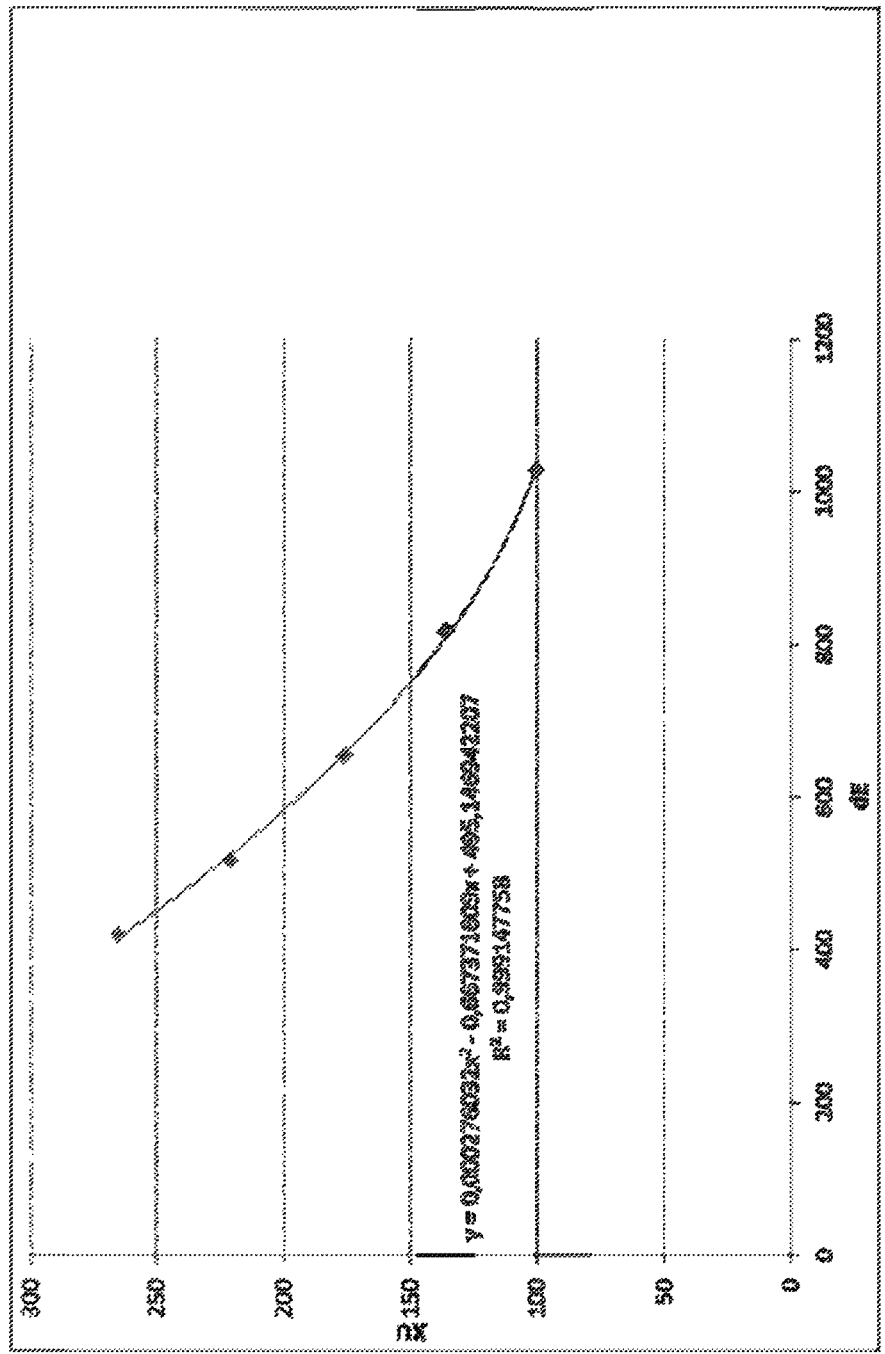
FIG. 5C shows a universal calibration curve in Laboratory C.
Figure 5D:
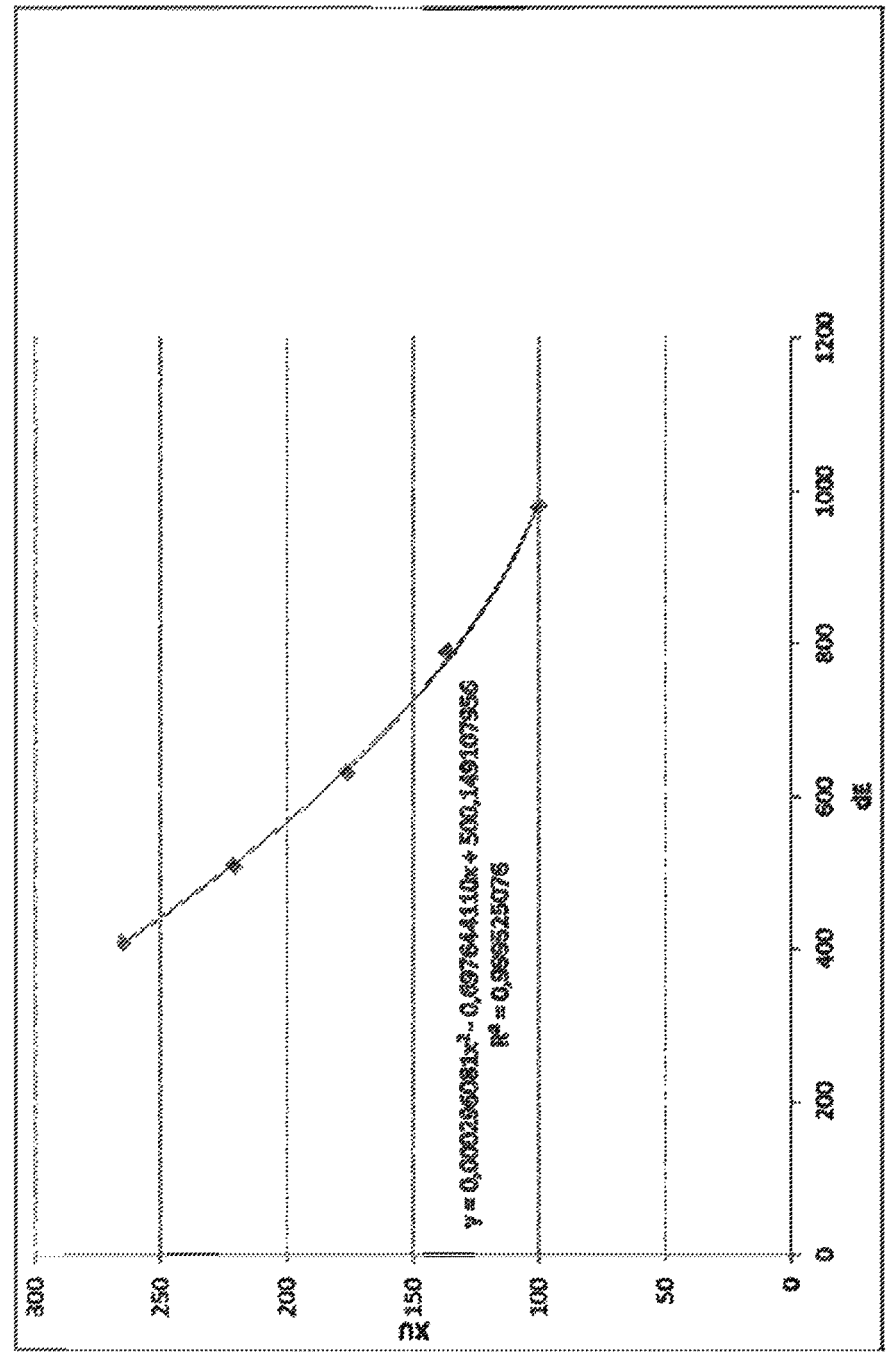
FIG. 5D shows a universal calibration curve in Laboratory D.

The present invention relates to a method for determining an anticoagulant activity elicited by a first anticoagulant in a sample of a subject comprising:

(a) measuring a first Factor Xa activity in a body fluid test sample of said subject;

(b) measuring a second Factor Xa activity in at least one calibrator sample comprising a predefined anticoagulation activity for a second anticoagulant;

(c) calculating an universal parameter for the anticoagulation activity comprised in the test sample based on the first and the second measured Factor Xa activities; and (d) comparing the said parameter for the anticoagulation activity with predefined ranges of expected anticoagulation activity for at least three anticoagulants in order to determine the anticoagulant activity.

The method of the present invention, preferably, is an ex vivo method, i.e. it is carried out in vitro with an isolated sample from a subject. Moreover, it may comprise steps in addition to those explicitly mentioned above. For example, further steps may relate to sample pre-treatments or evaluation of the results obtained by the method. The method may be carried out manually or assisted by automation. Steps (a), and/or (b) may in total or in part be assisted by automation, e.g., by a suitable robotic and sensory equipment for the determination in step (a) and/or (b), and a computer-implemented calculation or comparison algorithm on a data processing device in step (c) and (d), respectively. Preferably, at least steps c) and d) are carried out by a computer implemented algorithm.

The term "determining anticoagulant activity" as used in accordance with the present invention refers to qualitatively, quantitatively or semi-quantitatively determining the presence of anticoagulant activity in a sample of a subject. Anticoagulant activity refers to the capability of a compound to prevent or inhibit blood coagulation as set forth elsewhere herein in more detail.

The method of the present invention allows for determining quantitatively or semi-quantitatively the amount of anticoagulation activity present in a sample. Moreover, by comparing a parameter derived from the anticoagulation activity to predefined ranges of expected anticoagulation activity for given anticoagulants, the anticoagulant which elicits the anticoagulant activity in a sample can also be identified, i.e. the anticoagulant activity is determined (or identified) qualitatively.

The term "anticoagulant" as used herein refers to a compound which is capable of preventing or inhibiting blood coagulation. Blood coagulation is a well-known process wherein fibrin clots are formed by the blood in order to avoid blood loss from, e.g., damaged vessels. Blood coagulation is a process which involves a plurality of enzymes and auxiliary substances. For the formation of the fibrin clot, fibrinogen is converted into fibrin which subsequently becomes cross-linked. The fibrinogen as well as the enzyme which confers the cross linking, Factor XIIIa, are both enzymatically activated by the protease thrombin. Thrombin itself is activated by Factor Xa which again is activated by a Tissue Factor/Factor VIIa complex or a Factor IXa/Factor VIIIa complex. Factors VIIa, VIIIa and IXa are in turn also activated from their precursors during the blood coagulation process. Since the enzymes activate each other in a hierarchical order, the entirety of enzymes is sometimes also called the coagulation cascade. Various compounds have been described as anticoagulants which affect one or more enzymes or auxiliary substances of the coagulation cascade. Coumarins, e.g., are plant-derived vitamin k antagonists which deplete the organism of the active form of vitamin k which is required as auxiliary substance for thrombin and Factor VII, IX and X activity. Typical coumarins include warfarin, acenocoumarol, phenprocoumon, atromentin, brodifacoum or phenindione. Heparins are highly sulfated glycosaminoglycanes and resemble another class of naturally occurring anticoagulants. They activate antiprothrombin III which blocks the activity of thrombin and other enzymes of coagulation cascade including Factor Xa and, thereby, inhibit fibrin clot formation. Typically, low molecular weight heparin (LMWH) or unfractionated heparin (UFH) is used as heparin in anticoagulation therapy. Also heparanoids are used in anticoagulation therapy such as Danaparoid (also called Organ). Several drugs, such as Rivaroxaban or Apixaban, are reported to be direct Factor Xa inhibitors. Other Factor Xa inhibitors include Pentasaccharides such as Fondaparinux or Idraparinux. A first anticoagulant may, therefore, be an anticoagulant as defined above. The same applies for the second anticoagulant according to the invention. Preferably, however, said first and said second anticoagulants are different, i.e. a chemically different anticoagulant compounds. Preferably, said first and/or second anticoagulant is selected from the group consisting of: LMWH, UFH, Danaparoid, Rivaroxaban, Pentasaccharide, and Apixaban.

The term "body fluid test sample" as used herein refers to a body fluid sample which comprises anticoagulation activity. Preferably, said body fluid test sample is a urine sample, a whole blood sample or a blood plasma sample. Also encompassed are pre-treated body fluid samples such as citrated plasma samples.

The term "subject" as used herein refers to an animal having a coagulation system and, preferably, to a mammal and, more preferably, a human.

The term "calibrator sample" refers to a sample comprising predefined anticoagulation activity for a second anticoagulant which is used in the method of the present invention for calibration purposes. Calibrator samples can be obtained by making defined dilutions of a calibrator sample or a mother sample with predefined anticoagulation activity. Typically, the anticoagulation activity present in a calibrator sample is either known since it has been predefined or can be calculated without further ado. Preferably, a calibrator sample according to the present invention comprises predefined anticoagulation activity elicited by a second anticoagulant and, more preferably, a second anticoagulant selected from the group consisting of: LMWH, UFH, Danaparoid, Rivaroxaban, Pentasaccharide, and Apixaban. Preferably, the amount of anticoagulant used for the calibrator sample(s) is within the range which is also found in body fluid samples.

It will be understood that one or more calibrator samples with predefined anticoagulation activity for a second anticoagulant can be used in the method of the present invention for establishing a calibration. The term "at least one", thus, refers to one or more and, preferably, two, three, four, five, six, seven, eight, nine, ten or more calibrator samples which differ from each other in the predefined anticoagulation activity present in the said samples.

The term "Factor Xa" as used herein refers to an activated serine-endopeptidase which is capable of activating thrombin from prothrombin by proteolytic cleavage (E.C. 3.4.21.6). The enzyme is also known as the Stuart-Power-Factor or as prothrombinase. The structure of the enzyme is well known in various animal species including humans. The amino acid sequence of a human preproprotein of Factor Xa is deposited under NCBI Reference NP_000495.1 (GI: 4503625), a mouse amino acid sequence is deposited under NCBI Reference NP_001229297.1 (GI: 334724425). As discussed elsewhere herein, Factor Xa becomes activated from its precursor, Factor X, due to proteolytic cleavage by Tissue Factor/Factor VIIa complex or a Factor IXa/Factor VIIIa complex. It will be understood that the term also encompasses variants of such specific Factor Xa proteins. Such variants are proteins which differ in the amino acid sequence by at least one amino acid substitution, deletion and/or addition and which exhibit Factor Xa activity. The amino acid sequence of a variant Factor Xa is still, typically, at least 50%, 60%, 70%, 80%, 85%, 90%, 92%, 95%, 97%, 98%, or 99% identical with the amino sequence of the specific Factor Xa proteins referred to above. The degree of identity between two amino acid sequences can be determined by algorithms well known in the art. Preferably, the degree of identity is to be determined by comparing two optimally aligned sequences within a comparison window, such as the entire length of one of the amino acid sequences or at least 50% thereof, where the fragment of amino acid sequence in the comparison window may comprise additions or deletions (e.g., gaps or overhangs) as compared to the reference sequence for optimal alignment. The percentage is calculated by determining the number of positions at which the identical amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman 1981, Add. APL. Math. 2:482, by the homology alignment algorithm of Needleman and Wunsch 1970, J. Mol. Biol. 48:443, by the search for similarity method of Pearson and Lipman 1988, Proc. Natl. Acad Sci. (USA) 85: 2444, by computerized implementations of these algorithms (GAP, BESTFIT, BLAST, PASTA, and TFASTA in the Wisconsin Genetics Software Package, Genetics Computer Group (GCG), 575 Science Dr., Madison, Wis.), or by visual inspection. Given that two sequences have been identified for comparison, GAP and BESTFIT are preferably employed to determine their optimal alignment and, thus, the degree of identity. Preferably, the default values of 5.00 for gap weight and 0.30 for gap weight length are used. Variants referred to above may be allelic variants or any other species specific homologs, paralogs, or orthologs. Moreover, the variants referred to herein include fragments of Factor Xa or the aforementioned types of variants as long as these fragments have the essential the biological properties as referred to above. Such fragments may be, e.g., degradation products of the Factor Xa or chemically modified forms such as variants being posttranslationally modified. Moreover, variants include also genetically modified mutants of Factor Xa having, e.g., improved cleavage properties.

The term "Factor Xa activity" as used herein refers to the biological activity conferred by biologically active Factor Xa to a sample. A sample comprising biologically active Factor Xa is capable of activating thrombin by proteolytical cleavage of prothrombin. Factor Xa activity can be provided in a body fluid sample in accordance with the method of the present invention either as endogenously present Factor Xa activity or by exogenous supply of the sample with biologically active Factor Xa or a variant thereof as specified above. Also encompassed by the method of the present invention is a body fluid sample wherein the Factor Xa activity has been provided by exogenously supplementing the sample with a Factor X activating enzyme. Factor X activating enzymes which may be preferably applied include the endogenous activating enzymes of the blood coagulation cascade, such as Tissue Factor/Factor VIIa complex or a Factor IXa/Factor VIIIa complex, or other naturally occurring or genetically engineered Factor X activating enzymes, such as RVV-X from the Russel's viper venom or the venoms from Vipera lebetina, Bothrops spec., Akgistrodon spec, or Echis spec.

The term "measuring" as used herein refers to quantitatively assessing the Factor Xa activity present in a sample in the method of the present invention, i.e. the amount of Factor Xa activity in the sample is determined. Measuring Factor Xa activity can be achieved by detecting the amount of biologically active Factor Xa present in the said sample. Such detection can be, typically, made by an assay which directly or indirectly detects the Factor Xa activity. Since the decisive Factor Xa activity in accordance with the present invention is the capability to cleave prothrombin and, thus, the serine protease activity of Factor Xa, a suitable assay, preferably, aims at assessing the cleavage reaction of a substrate comprising a Factor Xa cleavage site by Factor Xa. Assessing the cleavage reaction may include the detection of the amount of cleaved substrate well as the velocity of the cleavage reaction. Both parameters allow for a quantitative assessment of the Factor Xa activity present in the sample. Moreover, the measurement of Factor Xa activity may also be made by directly detecting the amount of biologically active Factor Xa molecules present in the sample, e.g., by confirmation-specific antibodies or aptameres.

Preferably, said measuring the said Factor Xa activity in a sample in accordance with the present invention, however, comprises:
a) contacting said sample with reagents comprising at least Factor Xa and a Factor Xa substrate under conditions which allow for the enzymatic conversion of the substrate, whereby a physical or chemical property of the substrate is changed in a detectable manner; and
b) detecting the extent of the change of the physical or chemical property of the substrate; and
(c) comparing said extent of the change to a reference, whereby the Factor Xa activity in the sample is measured.

The term "reagents" refers to typically two reagents, one comprising biologically active Factor Xa and another which contains a substrate thereof, i.e. a Factor Xa substrate. The enzymatic conversion reaction of the Factor Xa substrate starts when both reagents are added to the sample and can be inhibited if anticoagulant activity is present in the sample. It is imaginable that both reagent components (i.e. FXa and the FXa substrate) could also be provided in one reagent, if appropriate means prevent the conversion of the substrate to take place before the plasma sample is added to the mixture.

It will be understood that the conditions referred to above may also typically include the addition of auxiliary compounds for the enzymatic conversion and/or the inhibition thereof by certain anticoagulants and/or the addition of stabilizing agents. Thereby, the components of the reaction mixture and/or the sample can be stabilized, the standardization or precision of the reaction or its sensitivity/specificity can be improved. One auxiliary compound may be antithrombin, which is an essential component for the action of heparins on Factor Xa. Other compounds might include dextrane sulfate, heparin antagonists such as polybrene or heparinase, stabilizers such as albumin, gelatin, glycin, other proteins, sugar molecules or any other compound which might improve stability of the reagents. Also antimicrobial substances may be added to prevent bacterial contamination or bacterial growth in the solution. Antioxidants or oxygen absorbers may also be applied.

The term "Factor Xa substrate" as used herein refers to a peptide or polypeptide or a non-peptide compound which is cleavable by the serine protease of biologically active Factor Xa. Peptide or Polypeptide Factor Xa substrates, preferably, comprise a Factor Xa recognition and cleavage site and can be obtained, e.g., by genetic engineering. Upon cleavage of the Factor Xa substrate by Factor Xa, at least one physical or chemical property of the substrate is changed. The term "physical or chemical property" as used herein encompasses physical properties such as molecular weight, size, density, magnetic resonance, polarization, optical density, viscosity, etc. as well as chemical properties such as fluorescence, resonance energy transfer properties, chromogenic properties, electrochemical properties, immunological properties or biochemical properties. Preferably, said physical or chemical property is selected from the group consisting of: fluorescence properties, optical properties and electrochemical properties. Typically, a Factor Xa substrate is, thus, a fluorogenic, chromogenic or amperogenic substrate. Fluorogenic or chromogenic substrates, usually, comprise a fluorophore or chromophore and a quenching moiety which are separated by a linker comprising a cleavage site for Factor Xa. In the uncleaved state, the quenching moiety suppresses fluorescence or color. Upon cleavage by Factor Xa, the quenching moiety can no longer suppress the fluorescence of the fluorophore or the color of the chromophore. Accordingly, the extent of fluorescence or color after cleavage can be correlated to the extent of Factor Xa activity exposed to the substrate. Other Factor Xa substrates may use resonance energy transfer between, e.g., a donor fluorophore and an acceptor. Upon cleavage, the resonance energy transfer can no longer be accomplished which results in a change of fluorescence. Again, the extent of the change correlates to the Factor Xa activity to which such a substrate is exposed to. Preferred substrates encompass chromogenic substrate S-2732 (Suc-Ile-Glu (gamma-pip)-Gly-Arg-pNA HCl), $CH_3SO_2$-D-Leu-Gly-Arg-pNA AcOH, $CH_3OCO$-D-CHG-Gly-Arg-pNA AcOH, $C_2H_5OCO$-D-Val-Gly-Arg-pNA AcOH, $CH_3OCO$-D-CHA-Gly-Arg-pNA AcOH, Cbo-Ile-Glu($\gamma$-OR)-Gly-Arg-pNA HCl, Cbo-D-Arg-Gly-Arg-pNA 2HCl or the fluorogenic substrates $CH_3SO_2$-D-CHA-Gly-Arg-AMC AcOH or Boc-Ile-Glu-Gly-Arg-AMC.

However as known to the ones skilled in the art many different substrates exist that can be used to detect FXa activity.

Detecting the extent of the change of the physical or chemical property of the substrate can be achieved by a suitable analyzer which is capable of detecting the change and its extent. Depending on the nature of the change of the physical or chemical property, different analyzers may be applied which are well known to the skilled person. Typically, an analyzer may, thus, rely on the measurement of signals of optical variables (e.g. absorbance or fluorescence), signals of electrical variables (e.g. resistance, capacitance, impedance, or combinations thereof), signals derived from magnetic resonance signals of the Factor Xa substrate in a cleaved and uncleaved state. Based on the change of the intensity of such a signal, the extent of the change may be determined which correlates to the efficiency of the enzymatic reaction and, thus, to the Factor Xa activity in the sample. It will be understood that the measured Factor Xa activity will be influenced by either the anticoagulant activity due to the presence of either the first or the second anticoagulant in a respective sample.

Calculating an universal parameter for the anticoagulation activity comprises comparing the first measured Factor Xa activity from the body fluid sample to the second measured Factor Xa activity from the at least one calibrator sample, wherein a calibration universal parameter for the Factor Xa activity has been allocated to the said second measured Factor Xa activity. Subsequently, a universal parameter for the anticoagulation activity comprised in the body fluid test sample can be derived from said calibration universal parameter(s). Preferably, the calibration universal parameter (P) is calculated by the following calculation: P=100+ (100*measured anticoagulation activity). The said calculation can be, preferably, carried out on a data processing device such as a computer having tangibly embedded a computer program code carrying out the said calculation automatically.

The universal parameter for the anticoagulation activity comprised in the body fluid sample will finally be compared with predefined ranges of expected anticoagulation activity for at least three anticoagulants. Depending on whether the universal parameter falls within the predefined range of one or more of the anticoagulants or is outside the ranges, a conclusion may be drawn as to the strength of the anticoagulant activity, the nature of the anticoagulant and/or the amount of anticoagulant which is present in the body fluid sample of the patient. Moreover, it is possible to calculate the Factor Xa activity specific for the anticoagulant and/or to determine the dosage of anticoagulant which may have been administered to a patient. Consequently, conclusions on anticoagulant therapy in a patient can be made by applying the method of the present invention. The comparison as well as a potential conclusion drawing can be, preferably, carried out on a data processing device such as a computer having tangibly embedded a suitable computer program code.

The predefined ranges are determined by analyzing samples from appropriate patient population. For example samples could be analyzed from patients that have received Rivaroxaban in a prophylactic dose, with the blood sampling taking place 2-3 hours after the last dose was taken by the patient. The resulting values would then be statistically analyzed, e.g. by determining the 95% confidence interval of the anticoagulant activity. The aforementioned analysis would provide the expected peak value of patients treated with Rivaroxaban in a prophylactic dose.

Another example would be an analysis of samples treated with LMWH in a specific dosage when the sampling is performed just before the application of the next LMWH dose. This analysis would provide the expected trough level of the anticoagulant activity in patients treated with LMWH in this specific dosage.

Preferably, the method of the present invention, therefore, also comprises the step of determining the dosage of first anticoagulant which has been administered to the subject based on the results of the determination in step (d). The said determination of the dosage can be, preferably, carried out on a data processing device such as a computer having tangibly embedded a computer program code carrying out the said determination automatically.

Particular preferred embodiments of the method of the present invention are described as follows:

In one particular embodiment of the method of the invention, the sample to be analyzed is citrated plasma. Said citrated plasma is contacted to a reaction mixture comprising Factor Xa and a chromogenic substrate and, in particular, S-2732. Typically, the said reaction mixture further comprises buffers and stabilizers. The enzymatic substrate conversion is typically measured by recording continuously the absorbance of the solution at 405 nm. A high rate of the conversion of the substrate by the Factor Xa results in a steep increase of the optical density which is expressed by the delta-E during the reaction (change of optical density during the reaction). A low rate of conversion results in a low delta-E. Depending on the inhibitory activity of the sample against the Factor Xa in the reagent, different absorption rates are detected. Four calibrator samples are preferably applied. Typically, said samples comprise 0, 0.5, 1 and 1.5 anti-Factor Xa units LMWH/ml calibrated against the current WHO LMWH standard. The calibrator samples may be provided in a premixed form or may be obtained by appropriate dilution of the calibrator sample having the highest LMWH concentration. The assigned values for the calibration are, preferably, 100 XU for the 0 anti-Xa unit/ml calibrator, 150 XU for the 0.5 anti-Xa unit/ml calibrator 200 XU for the 1 anti-Xa unit/ml calibrator and 250 XU for the 1.5 anti-Xa unit/ml calibrator, whereby "XU" stands for an arbitrary unit of anticoagulant activity directed against factor Xa. Using this calibration the results of the method are expressed in XU. If the sample contains little or no anticoagulant activity directed against Factor Xa, the XU is close to 100 and is increasingly higher in case that an activity against Factor Xa is present. When expected ranges of values for more than one anticoagulant are predefined, the anticoagulant activity can be assessed qualitatively and quantitatively by a comparison with the said expected ranges of values.

In a further particular preferred embodiment of the method of the invention, the anticoagulant amount administered to a subject can be calculated from the XU after the administered anticoagulant has been allocated to the determined XU values.

The mentioned algorithm for calculating the universal anticoagulant units results in typical test results of around 100 XU (no anticoagulant activity) and values increasing to values around 150 XU, 200 XU or even higher values for samples with anticoagulant activity. This unit system is easy to memorize, but on the other hand is not confused with INR values (as an expression of the prothrombin time) or aPTT results. However it is obvious that based on the inventive method also other unit systems could be defined, where e.g. the sample without anticoagulants could have results of 0 XU, 1 XU or 1000 XU, or any value in between.

It was surprisingly found in accordance with the present invention that it is possible to calibrate the result of Factor Xa inhibition assays against one anticoagulant, to express the results in arbitrary units, and to use this calibration also for assessing the activities of other anticoagulant drugs. Thereby, one receives a universal calibration technique which allows for standardizing the results of Factor Xa inhibition testing for a variety of drugs acting against this pathway. In addition it was found that it is possible at a later stage of the evaluation of the anticoagulant activity to calculate based on the results of the universal calibration the individual activity of the drug that corresponds to the universal Factor Xa inhibition activity which was measured, therefore allowing the physicians to calculate the drug activity based on the Factor Xa inhibition activity that was determined.

From a testing efficiency perspective, the inventive method has the advantage that it simplifies the workflow, as only one calibration is required for anti-Factor Xa testing, which means only one set of calibrators, one set of controls and one proficiency testing program is required. Also the ordering process is simplified, as only one test can be ordered (anti-Factor Xa-test), and not several different options (LMWH, UFH, Rivaroxabana, Apixaban, etc.). In addition, from a medical value perspective, risks are reduced, because the expression of the results of the assay procedure is as generic as the test procedure itself. In contrast, in the prior art, the expression of the assay results in a drug concentration that is more specific as the test itself, which can create misinterpretations and errors in case that a mistake is made at an early stage of the diagnostic process, i.e. when the test is ordered. With the inventive method the results are expressed as generic Factor Xa inhibition units, and therefore reflect what was measured, i.e. Factor Xa inhibition. In the prior art tests, e.g., a Rivaroxaban concentration could have been reported, although it is possible that the patient received Apixaban, a Pentasaccharide or any other drug inhibiting Factor Xa.

In the method of the present invention, what it is reported is more closely related to what was measured (i.e. Factor Xa inhibition). This eliminates the risk that a wrong ordering of the test early in the diagnostic chain propagates through the diagnostic process and finally leads to wrong information reported by the laboratory (e.g., a Rivaroxaban concentration, although the patient did not receive this drug). In accordance with the method of the present invention, it is still possible to express the results as drug concentrations, but this is decided later in the diagnostic chain and it is transparent to the phycisian which would select the drug in a laboratory information system and request to calculate the drug concentration from the anti-Factor Xa activity or this would happen automatically at the level of the hospital information system based on the drug prescription information available in the system.

The explanations and definitions of the terms given above apply mutatis mutandis for all following embodiments except if otherwise specified, below.

In a preferred method of the present invention, said method further comprises a step of recommending a therapeutic or diagnostic measure based on the determined anticoagulant activity.

The term "therapeutic measure" as used herein refers to any measure which influences or may be dependent on the coagulation status of the subject. Preferably, therapeutic measures include administration of drugs, adaptation of drug dosage, application of surgery, wound and injury management, adaptation of life style and/or nutrition and the like. The term "diagnostic measure" as used herein refers to any measure aiming at determining the coagulation status in a subject including the method of the present invention. Diagnostic measures include the selection of a diagnostic test as well as the decision on the frequency of diagnosis.

In another preferred method of the present invention, said method further comprises a step of applying a therapeutic or diagnostic measure based on the determined anticoagulant activity.

In yet another preferred method of the present invention, said method further comprises a step of managing the subject based on the determined anticoagulant activity.

The present invention also relates to a computer program code tangibly embedded on a data processor, said computer program code carrying out at least steps c) and d) of the method of the invention.

Moreover, the present invention relates to a system for determining an anticoagulant activity elicited by a first anticoagulant in a sample of a subject comprising:
(a) an analyzing unit capable of measuring Factor Xa activity in a sample of said subject and in at least one calibrator sample comprising a predefined anticoagulation activity for a second anticoagulant; and
(b) an evaluation unit comprising (i) a computer-implemented algorithm calculating an universal parameter for the anticoagulation activity comprised in the test sample based on the first and the second measured Factor Xa activities, and (ii) a computer-implemented algorithm comparing the said parameter for the anticoagulation activity with predefined ranges of expected anticoagulation activity for at least three anticoagulants.

The term "system" as used herein relates to an arrangement wherein the aforementioned units are operatively linked to each other such the determination of the anticoagulant activity can be achieved. The units may be comprised in separate housings or within a single housing. Both units shall preferably be operatively linked either by wire or in a wireless manner, e.g., via a wireless LAN, Bluetooth or via the internet. Accordingly, the units must not necessarily be in physical proximity. However, the operative linkage requires that the Factor Xa activity which is measured by the analyzing unit is transmitted into the evaluation unit such that the said evaluation unit can carry out the aforementioned evaluation steps on the basis of the transmitted Factor Xa activity data.

The analyzing unit according to the instant disclosure is, preferably, a stand-alone apparatus, or module within a larger instrument, which performs one or more of the detection, e.g. the measurement of the Factor Xa activity in quantitative and/or qualitative manner. For example, an analyzing unit may perform or assist with the pipetting, dosing, mixing of samples and/or reagents. An analyzing unit may comprise a reagent holding unit for holding reagents to perform the assays. Reagents may be arranged for example in the form of containers or cassettes containing individual reagents or group of reagents, placed in appropriate receptacles or positions within a storage compartment or conveyor. According to some embodiments, an analyzing unit may be configured for optical detection of an analyte, e.g. a chromogenic, fluorogenic or amperogenic substrate prior and/or after its enzymatic conversion by Factor Xa. An exemplary analyzing unit configured for optical detection comprises a device configured for converting electro-magnetic energy into an electrical signal, which includes both single and multi-element or array optical detectors. According to the present disclosure, an optical detector is capable of monitoring an optical electro-magnetic signal and providing an electrical outlet signal or response signal relative to a baseline signal indicative of the presence and/or concentration of an analyte in a sample being located in an optical path. Such devices may also include, for example, photodiodes, including avalanche photodiodes, phototransistors, photoconductive detectors, linear sensor arrays, CCD detectors, CMOS detectors, including CMOS array detectors, photomultipliers, and photomultiplier arrays. According to certain embodiments, an optical detector, such as a photodiode or photomultiplier, may contain additional signal conditioning or processing electronics. For example, an optical detector may include at least one pre-amplifier, electronic filter, or integrated circuit. Suitable pre-preamplifiers include, for example, integrating, transimpedance, and current gain (current mirror) pre-amplifiers. Additionally, one or more analyzing unit according to the instant disclosure may comprise a light source for emitting light. For example, a light source of an analyzing unit may consist of at least one light emitting element (such as a light emitting diode, an electric powered radiation source such as an incandescent lamp, an electroluminescent lamp, a gas discharge lamp, a high-intensity discharge lamp, a laser) for measuring analyte concentrations with a sample being tested or for enabling an energy transfer (for example, through florescent resonance energy transfer or catalyzing an enzyme). Further, an analyzing unit of the system may include one or more incubation units (for example, for contacting said sample with a reaction mixture comprising at least Factor Xa and a Factor Xa substrate under conditions which allow for the enzymatic conversion of the substrate, whereby a physical or chemical property of the substrate is changed in a detectable manner).

Additionally, an analyzing unit of the system disclosed herein may comprise, or be operationally connected to, a reaction vessel or cuvette feeding unit. Exemplary feeding units include liquid processing units, such as a pipetting unit, to deliver samples and/or reagents to the reaction vessels. The pipetting unit may comprise a reusable washable needle, e.g. a steel needle, or disposable pipette tips. The analyzing unit may further comprise one or more mixing units, for example a shaker to shake a cuvette comprising a liquid, or a mixing paddle to mix liquids in a cuvette, or reagent container.

The evaluation unit, typically, comprises a data processing device having implemented the aforementioned algorithms for calculating the universal parameter and for comparing it to the predefined ranges of expected anticoagulation activity for at least three anticoagulants. The said predefined ranges may be stored on a memory which, typically, is also comprised in the evaluation unit. A data processing device may be a general purpose computer or a portable computing device, for example. It should also be understood that multiple computing devices may be used together, such as over a network or other methods of transferring data, for performing one or more steps of the methods disclosed herein. Exemplary computing devices include desktop computers, laptop computers, personal data assistants ("PDA"), such as cellular devices, tablet computers, servers, and the like. In general, a data processing device comprises a processor capable of executing a plurality of instructions, such as an algorithm in the form of a computer program code. A data processing device, typically, has access to a memory. A memory is a computer readable medium and may comprise a single storage device or multiple storage devices, located either locally with the computing device or accessible to the computing device across a network, for example. Computer-readable media may be any available media that can be accessed by the computing device and includes both volatile and non-volatile media. Further, computer readable-media may be one or both of removable and non-removable media. By way of example, and not limitation, computer-readable media may comprise computer storage media. Exemplary computer storage media includes, but is not limited to, RAM, ROM, EEPROM, flash memory or any other memory technology, CD-ROM, Digital Versatile Disk (DVD) or other optical disk storage, magnetic cassettes, magnetic tape, magnetic disk storage or other magnetic storage devices, or any other medium which can be used for storing a plurality of instructions capable of being accessed by the data processing device and executed by the data processor of the said device.

Software typically present on the evaluation unit may, in general, include instructions which, when executed by a processor of the data processing device, may perform one or more steps of the methods disclosed herein. Some of the instructions may be adapted to produce signals that control operation of other machines and thus may operate through those control signals to transform materials far removed from the computer itself. The said instructions may also comprise an algorithm which is generally conceived to be a self-consistent sequence of steps leading to a desired result. These steps are those requiring physical manipulations of physical quantities. Usually, though not necessarily, these quantities take the form of electrical or magnetic pulses or signals capable of being stored, transferred, transformed, combined, compared, and otherwise manipulated. It proves convenient at times, principally for reasons of common usage, to refer to these signals as values, characters, display data, numbers, or the like as a reference to the physical items or manifestations in which such signals are embodied or expressed. It should be borne in mind, however, that all of these and similar terms are to be associated with the appropriate physical quantities and are merely used here as convenient labels applied to these quantities. According to some embodiments of the instant disclosure, algorithms for calculating the universal parameter and for comparing it to the predefined ranges of expected anticoagulation activity for at least three anticoagulants, are embodied and performed by executing the instructions. The data processing device may also have access to an output device. Exemplary output devices include fax machines, displays, printers, and files, for example. According to some embodiments of the present disclosure, a data processing device may perform one or more steps of a method disclosed herein, and thereafter provide an output, via an output device Preferably, the computer-implemented algorithm calculating an universal parameter for the anticoagulation activity is comparing the first measured Factor Xa activity to the second measured Factor Xa activity from the at least one calibrator sample, wherein a calibration universal parameter for the Factor Xa activity has been allocated to the said second measured Factor Xa activity, and is deriving the universal parameter for the anticoagulation activity comprised in the body fluid test sample from said calibration universal parameter.

Further, the present invention provides a kit for determining an anticoagulant activity elicited by a first anticoagulant in a sample comprising at least one calibrator sample comprising a predefined anticoagulation activity for a second anticoagulant and, preferably, Factor Xa and a Factor Xa substrate.

The term "kit" as used herein refers to a collection of the aforementioned components, preferably, provided separately or within a single container. The samples as well as the Factor Xa and Factor Xa substrate may be provided in the kit of the invention in a "ready-to-use" liquid form or in dry form, wherein the Factor Xa and Factor Xa substrate are provided in two separate containers, or in combination. In the latter case, addition of a solvent may be required in order to carry out the method of the invention. Suitable solvents are well known to the skilled person and may, preferably, also be included in the kit of the invention. The kit may further include controls, buffers, and/or reagents. The kit also comprises instructions for carrying out the method of the present invention, as well as information on the expected values for at least 3 anticoagulants. These instructions may be in the form of a manual, electronically accessible information or may be provided by a computer program code which is capable of carrying out the calculations and comparisons referred to in the methods of the present invention and to establish a determination of anticoagulant activity when implemented on a computer or a data processing device. The computer program code may be provided on a data storage medium or device such as an optical storage medium (e.g., a Compact Disc) or directly on a computer or data processing device. A further aspect of the invention pertains to a method, computer program code, system or kit as described above wherein Factor IIa activity is measured rather than Factor Xa activity.

Therefore, also encompassed by the invention is a method for determining an anticoagulant activity elicited by a first anticoagulant in a sample of a subject comprising:
(a) measuring a first Factor IIa activity in a body fluid test sample of said subject;
(b) measuring a second Factor IIa activity in at least one calibrator sample comprising a predefined anticoagulation activity for a second anticoagulant;
(c) calculating an universal parameter for the anticoagulation activity comprised in the test sample based on the first and the second measured Factor IIa activities;
(d) comparing the said parameter for the anticoagulation activity with predefined ranges of expected anticoagulation activity for at least three anticoagulants in order to determine the anticoagulant activity.

The term "Factor IIa" as used herein refers to an activated serine-endopeptidase which is capable of activating fibrinogen to fibrin by proteolytic cleavage (E.C. 3.4.21.5). Moreover, the enzyme is furthermore capable of converting Factors XI to XIa, VIII to VIIIa, and V to Va. The enzyme is also known as Thrombin. The structure of the enzyme is well known in various animal species including humans. The amino acid sequence of a human preproprotein of Thrombin is deposited under NCBI Reference NP_000497.1 (GI: 4503635), a mouse amino acid sequence is deposited under NCBI Reference NP_034298.1 (GI: 6753798). As discussed elsewhere herein, Thrombin becomes activated from its precursor, Prothrombin, due to proteolytic cleavage by Factor Xa. It will be understood that the term also encompasses variants of such specific Thrombin proteins. Such variants are proteins which differ in the amino acid sequence by at least one amino acid substitution, deletion and/or addition and which exhibit Thrombin activity. The amino acid sequence of a variant Thrombin is still, typically, at least 50%, 60%, 70%, 80%, 85%, 90%, 92%, 95%, 97%, 98%, or 99% identical with the amino sequence of the specific Thrombin proteins referred to above. The degree of identity between two amino acid sequences can be determined by algorithms well known in the art. Preferably, the degree of identity is to be determined by comparing two optimally aligned sequences within a comparison window, such as the entire length of one of the amino acid sequences or at least 50% thereof, where the fragment of amino acid sequence in the comparison window may comprise additions or deletions (e.g., gaps or overhangs) as compared to the reference sequence for optimal alignment. The percentage is calculated by determining the number of positions at which the identical amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman 1981, Add. APL. Math. 2:482, by the homology alignment algorithm of Needleman and Wunsch 1970, J. Mol. Biol. 48:443, by the search for similarity method of Pearson and Lipman 1988, Proc. Natl. Acad Sci. (USA) 85: 2444, by computerized implementations of these algorithms (GAP, BESTFIT, BLAST, PASTA, and TFASTA in the Wisconsin Genetics Software Package, Genetics Computer Group (GCG), 575 Science Dr., Madison, Wis.), or by visual inspection. Given that two sequences have been identified for comparison, GAP and BESTFIT are preferably employed to determine their optimal alignment and, thus, the degree of identity. Preferably, the default values of 5.00 for gap weight and 0.30 for gap weight length are used. Variants referred to above may be allelic variants or any other species specific homologs, paralogs, or orthologs. Moreover, the variants referred to herein include fragments of Thrombin or the aforementioned types of variants as long as these fragments have the essential the biological properties as referred to above. Such fragments may be, e.g., degradation products of the Thrombin or chemically modified forms such as variants being posttranslationally modified. Moreover, variants include also genetically modified mutants of Thrombin having, e.g., improved cleavage properties.

The term "Factor IIa or Thrombin activity" as used herein refers to the biological activity conferred by biologically active Thrombin to a sample. A sample comprising biologically active Thrombin is capable of activating fibrin from fibrinogen by proteolytical cleavage. Thrombin activity can be provided in a body fluid sample in accordance with the method of the present invention either as endogenously present Thrombin activity or by exogenous supply of the sample with biologically active Thrombin or a variant thereof as specified above. Also encompassed by the method of the present invention is a body fluid sample wherein the Thrombin activity has been provided by exogenously supplementing the sample with a Thrombin activating enzyme. Thrombin activating enzymes which may be preferably applied include the endogenous activating enzymes of the blood coagulation cascade, such as Factor Xa.

In a preferred embodiment of the aforementioned method, said first and said second anticoagulants are different.

In a preferred embodiment of any the aforementioned methods, said measuring the said Factor IIa activity in a sample comprises:

a) contacting said sample with a reaction mixture comprising at least Factor IIa and a Factor IIa substrate under conditions which allow for the enzymatic conversion of the substrate, whereby a physical or chemical property of the substrate is changed in a detectable manner; and
b) detecting the extent of the change of the physical or chemical property of the substrate; and
(c) comparing said extent of the change to a reference, whereby the amount of anti-Factor IIa activity in the sample is measured. More preferably, said physical or chemical property is selected from the group consisting of: fluorescence properties, optical properties and electrochemical properties.

Preferred substrates encompass chromogenic substrates Bz-FVR-pNA, H-D-Phe-Homopro-Arg-pNA•2 acetate, Sar-Pro-Arg-pNA, Tos-Gly-Pro-Arg-pNA•AcOH, H-D-CHG-Ala-Arg-pNA•2AcOH, H-D-CHG-But-Arg-pNA•2AcOH, H-D-CHG-Pro-Arg-pNA•2AcOH, H-D-CHA-Ala-Arg-pNA•2AcOH, H-D-CHA-Gly-Arg-pNA•2AcOH or $CH_3OCO$-Gly-Pro-Arg-pNA•AcOH as well as the fluorogenic substrates Boc-Val-Arg-AMC•HCl, Boc-VPR-AMC, Bz-FVR-AMC or H-D-CHA-Ala-Arg-AMC•2AcOH.

However as known to the ones skilled in the art many different substrates exist that can be used to detect FXa activity.

In a further preferred embodiment of any the aforementioned methods, said subject is a mammal and, preferably, a human.

In yet a preferred embodiment of any the aforementioned methods, wherein said body fluid test sample is a urine sample, a whole blood sample or a blood plasma sample.

In a preferred embodiment of any the aforementioned methods, said calculating an universal parameter for the anticoagulation activity comprises comparing the first measured Factor IIa activity to the second measured Factor IIa activity from the at least one calibrator sample, wherein a calibration universal parameter for the anti-Factor IIa activity has been allocated to the said second measured Factor IIa activity, and deriving the universal parameter for the anticoagulation activity comprised in the body fluid test sample from said calibration universal parameter. More preferably, the assigned universal parameter (P) is calculated by the following calculation: P=100+(factor*amount or activity of the anticoagulant used for the calibration).

The factor should be selected in a way, that a typical therapeutic dose of the anticoagulant would provide an universal anticoagulation parameter of 200 IIU (arbitrary units of anti-Factor IIa activity).

In a preferred embodiment of any the aforementioned methods, said first and/or second anticoagulant is selected from the group consisting of: recombinant hirudin, dabidatran, argatroban and bivalirudin.

In another preferred embodiment of any the aforementioned methods, at least steps c) and d) are carried out by a computer implemented algorithm.

Further encompassed is a computer program code tangibly embedded on a data processor, said computer program code carrying out at least steps c) and d) of any one of the aforementioned methods.

Moreover, a system is encompassed for determining an anticoagulant activity elicited by a first anticoagulant in a sample of a subject comprising:
(a) an analyzing unit capable of measuring Factor IIa activity in a sample of said subject and in at least one calibrator sample comprising a predefined anticoagulation activity for a second anticoagulant; and
(b) an evaluation unit comprising (i) a computer-implemented algorithm calculating an universal parameter for the anticoagulation activity comprised in the test sample based on the first and the second measured Factor IIa activities, and (ii) a computer-implemented algorithm comparing the said parameter for the anticoagulation activity with predefined ranges of expected anticoagulation activity for at least three anticoagulants.

In a preferred embodiment of the aforementioned system, said computer-implemented algorithm calculating an universal parameter for the anticoagulation activity is comparing the first measured Factor IIa activity to the second measured Factor IIa activity from the at least one calibrator sample, wherein a calibration universal parameter for the Factor IIa activity has been allocated to the said second measured Factor IIa activity, and is deriving the universal parameter for the anticoagulation activity comprised in the body fluid test sample from said calibration universal parameter.

Finally provided is a kit for determining an anticoagulant activity elicited by a first anticoagulant in a sample comprising at least one calibrator sample comprising a predefined anticoagulation activity for a second anticoagulant and, preferably, Factor IIa and a Factor IIa substrate.

All references cited in this specification are herewith incorporated by reference with respect to their entire disclosure content and the disclosure content specifically mentioned in this specification.

EXAMPLES

The following Examples shall merely illustrate the invention or aspects thereof. They must, however, not be construed in any way which limits the scope of the invention.

Example 1: Evaluation for the Universal Calibration Concept (Unitest) for Factor Xa Antagonists The aim of the study was to show that the universal calibration allows to monitor several different anticoagulants directed against Factor Xa using one single calibration curve, instead of the current state of the art with several calibration curves. It shall also be shown that it is possible to transform the results of the universal calibration into the actual drug concentrations.

Control samples for 3 different anticoagulants (low molecular weight heparin, Rivaroxaban=Xarelto®, Danaparoid=Orgaran®) were sent to 4 laboratories and were analyzed in duplicate on 3 days. On day 1 also calibration curves for the individual anticoagulants were determined.

In addition to calculating the individual calibrations also a universal calibration was determined.

In the following it is assessed whether the universal calibration provides as good an agreement over the three centers compared to the individual calibrations.

The following calibrators were sent to the labs and assayed on day 1:

TABLE 1

List of Calibrators for the different laboratories

| Calibrator | | Assigned concentration | |
|---|---|---|---|
| Heparin Calibrator | Cal1 | 0 | aXa U/ml |
| Heparin Calibrator | Cal2 | 0.36 | aXa U/ml |
| Heparin Calibrator | Cal3 | 0.76 | aXa U/ml |
| Heparin Calibrator | Cal4 | 1.21 | aXa U/ml |
| Heparin Calibrator | Cal5 | 1.65 | aXa U/ml |
| Rivaroxaban Calibrator | Cal1 | 0 | µg/ml |
| Rivaroxaban Calibrator | Cal2 | 0.25 | µg/ml |
| Rivaroxaban Calibrator | Cal3 | 0.49 | µg/ml |
| Orgaran Calibrator | Cal1 | 0 | Orgaran U/ml |
| Orgaran Calibrator | Cal2 | 0.4 | Orgaran U/ml |
| Orgaran Calibrator | Cal3 | 0.8 | Orgaran U/ml |
| Orgaran Calibrator | Cal4 | 1.2 | Orgaran U/ml |
| Orgaran Calibrator | Cal5 | 1.6 | Orgaran U/ml |

The following controls were sent to the labs and analyzed on days 1-3:

TABLE 2

List of controls for the different laboratories

| Control | | Assigned concentration | |
|---|---|---|---|
| Control Normal | Verum | 0 | aXa U/ml |
| LMWH Control | CI | 0.25 | aXa U/ml |
| LMWH Control | CII | 0.48 | aXa U/ml |
| LMWH Control | C3 | 0.8 | aXa U/ml |
| LMWH Control | C4 | 1.2 | aXa U/ml |
| Rivaroxaban Control | C1 | 0.09 | µg/ml |
| Rivaroxaban Control | C2 | 0.3 | µg/ml |
| Orgaran Control | C1 | 0.48 | Orgaran U/ml |
| Orgaran Control | C2 | 1 | Orgaran U/ml |

The assay was carried out as follows:

The samples were reconstituted before the analysis. The sample was added to a solution containing bovine Factor Xa and to a second solution containing the chromogenic substrate S-2732 (Suc-Ile-Glu (gamma-pip)-Gly-Arg-pNA, HCl). The optical density of the solution is measured and the change of optical density is reported. The assayed plasma calibrators and controls were commercially obtained from Hyphen biomed, the anti-Xa assay is commercially available from Instrumentation Laboratory.

A universal calibration was determined using the LMWH calibrators. Calibration was performed in arbitrary units called "XU". The relation of assigned aXa U/ml to XU was as follows:

Anticoagulant activity in XU=100+100*anticoagulant activity in aXa U/ml; see FIG. 1.

The samples sent to the laboratories were analyzed on three separate days and results were reported.

TABLE 3

Raw data of the calibrations

| | | Laboratory A | | Laboratory B | | Laboratory C | | Laboratory D | |
|---|---|---|---|---|---|---|---|---|---|
| | | dE1 | dE2 | dE1 | dE2 | dE1 | dE2 | dE1 | dE2 |
| Heparin | Cal1 | 1039 | 1033 | 1505 | 1478 | 1022 | 1035 | 989 | 973 |
| Heparin | Cal2 | 821 | 833 | 1223 | 1168 | 817 | 820 | 796 | 783 |
| Heparin | Cal3 | 646 | 667 | 967 | 980 | 642 | 667 | 633 | 631 |
| Heparin | Cal4 | 508 | 494 | 770 | 788 | 512 | 525 | 508 | 511 |
| Heparin | Cal5 | 415 | 396 | 649 | 658 | 427 | 414 | 419 | 400 |
| Rivaroxaban | Cal1 | 1073 | 1078 | 1555 | 1498 | 1039 | 1040 | 988 | 997 |
| Rivaroxaban | Cal2 | 220 | 221 | 302 | 273 | 205 | 204 | 221 | 215 |

TABLE 3-continued

| | | Laboratory A | | Laboratory B | | Laboratory C | | Laboratory D | |
|---|---|---|---|---|---|---|---|---|---|
| | | dE1 | dE2 | dE1 | dE2 | dE1 | dE2 | dE1 | dE2 |
| Rivaroxaban | Cal3 | 80 | 79 | 121 | 112 | 87 | 85 | 91 | 94 |
| Orgaran | Cal1 | 1074 | 1065 | 1578 | 1533 | 1036 | 1044 | 1011 | 1002 |
| Orgaran | Cal2 | 766 | 781 | 1146 | 1156 | 755 | 790 | 738 | 736 |
| Orgaran | Cal3 | 555 | 549 | 868 | 895 | 577 | 597 | 550 | 536 |
| Orgaran | Cal4 | 425 | 420 | 724 | 692 | 453 | 473 | 445 | 428 |
| Orgaran | Cal5 | 338 | 328 | 558 | 567 | 360 | 380 | 343 | 351 |

TABLE 4

Raw data of the controls

| | Control day | Normal | LMWH Control | | | | Rivaroxaban c. | | Orgaran c. | |
|---|---|---|---|---|---|---|---|---|---|---|
| | | | CI | CII | C3 | C4 | C1 | C2 | C1 | C2 |
| Laboratory A | 1 | 1094 | 878 | 748 | 639 | 494 | 558 | 181 | 724 | 499 |
| Laboratory A | 1 | 1085 | 885 | 733 | 604 | 483 | 582 | 175 | 718 | 491 |
| Laboratory A | 2 | 1038 | 838 | 721 | 612 | 479 | 547 | 174 | 708 | 465 |
| Laboratory A | 2 | 1076 | 850 | 752 | 629 | 500 | 564 | 168 | 699 | 471 |
| Laboratory A | 3 | 1082 | 874 | 744 | 622 | 494 | 585 | 168 | 707 | 462 |
| Laboratory A | 3 | 1076 | 873 | 751 | 624 | 499 | 585 | 182 | 711 | 472 |
| Laboratory B | 1 | 1512 | 1249 | 1115 | 958 | 713 | 818 | 234 | 1076 | 771 |
| Laboratory B | 1 | 1517 | 1307 | 1109 | 951 | 761 | 864 | 235 | 1037 | 734 |
| Laboratory B | 2 | 1497 | 1311 | 1086 | 922 | 738 | 911 | 228 | 1066 | 753 |
| Laboratory B | 2 | 1452 | 1267 | 1097 | 956 | 759 | 851 | 235 | 1021 | 779 |
| Laboratory B | 3 | 1481 | 1310 | 1113 | 950 | 784 | 847 | 224 | 1047 | 755 |
| Laboratory B | 3 | 1480 | 1270 | 1111 | 941 | 764 | 827 | 233 | 1075 | 754 |
| Laboratory C | 1 | 1067 | 859 | 631 | 569 | 521 | 568 | 157 | 717 | 496 |
| Laboratory C | 1 | 1070 | 887 | 652 | 636 | 496 | 565 | 164 | 702 | 494 |
| Laboratory C | 2 | 1062 | 874 | 760 | 634 | 510 | 555 | 160 | 694 | 503 |
| Laboratory C | 2 | 1054 | 850 | 745 | 626 | 499 | 557 | 161 | 699 | 503 |
| Laboratory C | 3 | 1058 | 869 | 747 | 619 | 512 | 577 | 159 | 718 | 501 |
| Laboratory C | 3 | 1063 | 869 | 741 | 643 | 517 | 576 | 168 | 722 | 516 |
| Laboratory D | 1 | 1023 | 819 | 722 | 613 | 492 | 572 | 181 | 682 | 488 |
| Laboratory D | 1 | 1020 | 815 | 721 | 613 | 484 | 563 | 178 | 686 | 477 |
| Laboratory D | 2 | 1030 | 841 | 730 | 608 | 479 | 526 | 177 | 687 | 476 |
| Laboratory D | 2 | 1017 | 841 | 726 | 613 | 487 | 579 | 178 | 702 | 489 |
| Laboratory D | 3 | 1032 | 840 | 735 | 616 | 492 | 596 | 179 | 692 | 496 |
| Laboratory D | 3 | 1023 | 819 | 724 | 613 | 485 | 574 | 181 | 691 | 492 |

TABLE 5

Means and coefficients of variations of the raw signal (mE) of the controls

| | | Mean raw signal | cv |
|---|---|---|---|
| Control Normal | | 1163 | 16.7% |
| LMWH Control | CI | 962 | 20.0% |
| LMWH Control | CII | 821 | 20.7% |
| LMWH Control | C3 | 700 | 20.8% |
| LMWH Control | C4 | 560 | 20.5% |
| Rivaroxaban Control | C1 | 639 | 20.0% |
| Rivaroxaban Control | C2 | 187 | 14.7% |
| Orgaran Control | C1 | 791 | 19.7% |
| Orgaran Control | C2 | 556 | 21.6% |

This explains the need why a calibration is required in the first place. Even though the same batch of reagent was applied by all four centers, still CVs of around 20% were determined for the analyses of the same controls, simply due to differences between the instruments applied in the centers.

The results for different calibrations and laboratories are shown in FIGS. 2 to 5. FIG. 2 shows calibration curves for the 4 laboratories for heparin, FIG. 3 for Rivaroxaban, and FIG. 4 for Orgaran. FIG. 5 shows the universal calibration curves established in the 4 laboratories.

TABLE 6

Regression curves and $R^2$ values for the different calibrations shown in FIGS. 2 to 5

| Laboratory | Calibration | Regression Curve (x: raw signal) | $R^2$ |
|---|---|---|---|
| Laboratory A | Heparin | $-1.744\ln(x) + 12.083$ | 0.9981 |
| Laboratory A | Rivaroxaban | $0.892690309e^{-0.006300096x}$ | 0.998984101 |
| Laboratory A | Orgaran | $0.000002228x^2 - 0.005216221x + 3.045990443$ | 0.994439120 |

TABLE 6-continued

Regression curves and $R^2$ values for the different calibrations shown in FIGS. 2 to 5

| Laboratory | Calibration | Regression Curve (x: raw signal) | $R^2$ |
|---|---|---|---|
| Laboratory A | Unitest | $0.000233896x^2 - 0.592434149x + 463.666010062$ | 0.997898826 |
| Laboratory B | Heparin | $0.000001496x^2 - 0.005139085x + 4.344124193$ | 0.998464567 |
| Laboratory B | Rivaroxaban | $0.851889038e^{-0.004416733x}$ | 0.999851520 |
| Laboratory B | Organan | $0.000001172x^2 - 0.004072431x + 3.505349835$ | 0.998817817 |
| Laboratory B | Unitest | $0.000149639x^2 - 0.513908541x + 534.412419251$ | 0.998464567 |
| Laboratory C | Heparin | $0.000002760x^2 - 0.006673716x + 3.951469422$ | 0.999147758 |
| Laboratory C | Rivaroxaban | $0.901449676e^{-0.006537153x}$ | 0.999769218 |
| Laboratory C | Organan | $0.000002495x^2 - 0.005857423x + 3.401949500$ | 0.998193391 |
| Laboratory C | Unitest | $0.000276032x^2 - 0.667371609x + 495.146942207$ | 0.999147758 |
| Laboratory D | Heparin | $0.000002961x^2 - 0.006976441x + 4.001491080$ | 0.999525076 |
| Laboratory D | Rivaroxaban | $1.025044113e^{-0.006971051x}$ | 0.999108005 |
| Laboratory D | Organan | $0.000002852x^2 - 0.006224104x + 3.387947938$ | 0.996263341 |
| Laboratory D | Unitest | $0.000296081x^2 - 0.697644110x + 500.149107956$ | 0.999525076 |

TABLE 7

Determined anticoagulant concentrations

| center | day | Control Normal | LMWH Control CI | LMWH Control CII | LMWH Control C3 | LMWH Control C4 | Rivar. Control C1 | Rivar. Control C2 | Organan Control C1 | Organan Control C2 |
|---|---|---|---|---|---|---|---|---|---|---|
| target value | | 0 | 0.25 | 0.48 | 0.8 | 1.2 | 0.09 | 0.3 | 0.48 | 1 |
| A | 1 | −0.12 | 0.26 | 0.54 | 0.82 | 1.27 | 0.03 | 0.29 | 0.44 | 1.00 |
| A | 1 | −0.11 | 0.25 | 0.58 | 0.92 | 1.31 | 0.02 | 0.30 | 0.45 | 1.02 |
| A | 2 | −0.03 | 0.34 | 0.61 | 0.89 | 1.32 | 0.03 | 0.30 | 0.47 | 1.10 |
| A | 2 | −0.09 | 0.32 | 0.53 | 0.84 | 1.24 | 0.03 | 0.31 | 0.49 | 1.08 |
| A | 3 | −0.10 | 0.27 | 0.55 | 0.86 | 1.27 | 0.02 | 0.31 | 0.47 | 1.11 |
| A | 3 | −0.09 | 0.27 | 0.53 | 0.86 | 1.25 | 0.02 | 0.28 | 0.46 | 1.08 |
| B | 1 | −0.01 | 0.26 | 0.47 | 0.79 | 1.44 | 0.02 | 0.30 | 0.48 | 1.06 |
| B | 1 | −0.01 | 0.18 | 0.48 | 0.81 | 1.30 | 0.02 | 0.30 | 0.54 | 1.15 |
| B | 2 | 0.00 | 0.18 | 0.53 | 0.88 | 1.37 | 0.02 | 0.31 | 0.50 | 1.10 |
| B | 2 | 0.04 | 0.23 | 0.51 | 0.80 | 1.31 | 0.02 | 0.30 | 0.57 | 1.04 |
| B | 3 | 0.01 | 0.18 | 0.48 | 0.81 | 1.23 | 0.02 | 0.32 | 0.53 | 1.10 |
| B | 3 | 0.02 | 0.23 | 0.48 | 0.83 | 1.29 | 0.02 | 0.30 | 0.48 | 1.10 |
| C | 1 | −0.03 | 0.26 | 0.84 | 1.05 | 1.23 | 0.02 | 0.32 | 0.48 | 1.11 |
| C | 1 | −0.03 | 0.20 | 0.77 | 0.82 | 1.32 | 0.02 | 0.31 | 0.52 | 1.12 |
| C | 2 | −0.02 | 0.23 | 0.47 | 0.83 | 1.27 | 0.02 | 0.32 | 0.54 | 1.09 |
| C | 2 | −0.02 | 0.27 | 0.51 | 0.86 | 1.31 | 0.02 | 0.31 | 0.53 | 1.09 |
| C | 3 | −0.02 | 0.24 | 0.51 | 0.88 | 1.26 | 0.02 | 0.32 | 0.48 | 1.09 |
| C | 3 | −0.02 | 0.24 | 0.52 | 0.80 | 1.24 | 0.02 | 0.30 | 0.47 | 1.04 |
| D | 1 | −0.04 | 0.27 | 0.51 | 0.84 | 1.29 | 0.02 | 0.29 | 0.47 | 1.03 |
| D | 1 | −0.03 | 0.28 | 0.51 | 0.84 | 1.32 | 0.02 | 0.30 | 0.46 | 1.07 |
| D | 2 | −0.04 | 0.23 | 0.49 | 0.86 | 1.34 | 0.03 | 0.30 | 0.46 | 1.07 |
| D | 2 | −0.03 | 0.23 | 0.50 | 0.84 | 1.31 | 0.02 | 0.30 | 0.42 | 1.03 |
| D | 3 | −0.04 | 0.23 | 0.47 | 0.83 | 1.29 | 0.02 | 0.29 | 0.45 | 1.00 |
| D | 3 | −0.04 | 0.27 | 0.50 | 0.84 | 1.32 | 0.02 | 0.29 | 0.45 | 1.02 |
| mean | | −0.04 | 0.25 | 0.54 | 0.85 | 1.29 | 0.02 | 0.30 | 0.48 | 1.07 |
| cv | | | 16.3% | 16.7% | 6.1% | 3.7% | 14.9% | 3.5% | 7.5% | 3.8% |
| average CV | | 9.0% | | | | | | | | |

The analysis shows the individual results, the mean values, and the CVs of the 24 measurements that were performed for each control (4 laboratories, 3 days, 2 determinations each).

The analysis also reveals a problem of the classical strategy to calibrate the individual drugs: samples without anticoagulant can easily become negative, which is typically reported as 0 or <0.05 aXa U/ml (for example). Still this may cause mathematical problems when, e.g., results of clinical trials are statistically analyzed.

TABLE 8

Results of the measurements using the universal calibration

| Unit | | Control Normal XU | LMWH Control CI XU | LMWH Control CII XU | LMWH Control C3 XU | LMWH Control C4 XU | Rivar. Control C1 XU | Rivar. Control C2 XU | Organan Control C1 XU | Organan Control C2 XU |
|---|---|---|---|---|---|---|---|---|---|---|
| center | day | | | | | | | | | |
| A | 1 | 95 | 124 | 151 | 181 | 228 | 206 | 364 | 157 | 226 |
| A | 1 | 96 | 123 | 155 | 191 | 232 | 198 | 367 | 159 | 229 |
| A | 2 | 101 | 132 | 158 | 189 | 233 | 210 | 368 | 162 | 239 |
| A | 2 | 97 | 129 | 150 | 183 | 226 | 204 | 370 | 164 | 236 |
| A | 3 | 97 | 125 | 152 | 186 | 228 | 197 | 371 | 162 | 240 |
| A | 3 | 97 | 125 | 151 | 185 | 226 | 197 | 363 | 161 | 236 |
| B | 1 | 99 | 126 | 147 | 179 | 244 | 214 | 422 | 155 | 227 |
| B | 1 | 99 | 118 | 149 | 181 | 230 | 202 | 422 | 162 | 238 |
| B | 2 | 100 | 118 | 153 | 188 | 237 | 190 | 425 | 157 | 232 |
| B | 2 | 104 | 124 | 151 | 180 | 231 | 205 | 422 | 166 | 225 |
| B | 3 | 102 | 118 | 148 | 181 | 223 | 206 | 427 | 160 | 232 |
| B | 3 | 102 | 123 | 148 | 183 | 229 | 212 | 423 | 155 | 232 |
| C | 1 | 97 | 126 | 184 | 205 | 223 | 205 | 397 | 159 | 232 |
| C | 1 | 97 | 120 | 177 | 183 | 232 | 206 | 393 | 163 | 233 |
| C | 2 | 98 | 123 | 147 | 183 | 227 | 210 | 395 | 165 | 229 |
| C | 2 | 98 | 127 | 151 | 186 | 231 | 209 | 395 | 163 | 229 |
| C | 3 | 98 | 124 | 151 | 188 | 226 | 202 | 396 | 158 | 230 |
| C | 3 | 98 | 124 | 152 | 180 | 224 | 202 | 391 | 157 | 224 |
| D | 1 | 96 | 127 | 151 | 184 | 229 | 198 | 384 | 162 | 230 |
| D | 1 | 97 | 128 | 151 | 184 | 232 | 201 | 385 | 161 | 235 |
| D | 2 | 96 | 123 | 149 | 186 | 234 | 215 | 386 | 161 | 235 |
| D | 2 | 97 | 123 | 150 | 184 | 231 | 195 | 385 | 156 | 230 |
| D | 3 | 95 | 123 | 147 | 183 | 229 | 190 | 385 | 159 | 227 |
| D | 3 | 96 | 127 | 150 | 184 | 232 | 197 | 384 | 159 | 229 |
| mean | | 98.02 | 124.07 | 153.08 | 184.78 | 229.76 | 203.04 | 392.51 | 160.09 | 231.47 |
| cv | | 2.2% | 2.7% | 5.8% | 2.8% | 2.0% | 3.4% | 5.3% | 1.9% | 1.9% |
| average CV | | 3.2% | | | | | | | | |

The analysis shows significantly better CVs for using universal calibrations compared to the expression of results by the anticoagulant concentration (prior art). Also the problem of the expression of results without anticoagulant activity does not occur.

Example 2: Determination of Anticoagulant Activity Based on Universal Calibration

TABLE 9

Calibration curves from the 4 laboratories for all three anticoagulants. The calibration curves are shown as raw data (delta-E = dE) and expressed in XU (universal calibration = Unitest).

| | | Heparin Calibrator | | | | | Rivar. Calibrator | | | Organan Calibrator | | | | |
|---|---|---|---|---|---|---|---|---|---|---|---|---|---|---|
| | | Cal1 | Cal2 | Cal3 | Cal4 | Cal5 | Cal1 | Cal2 Target | Cal3 | Cal1 | Cal2 | Cal3 | Cal4 | Cal5 |
| Center | | 0 | 0.36 | 0.76 | 1.21 | 1.65 | 0 | 0.25 | 0.49 | 0 | 0.4 | 0.8 | 1.2 | 1.6 |
| | | | | aXa U/ml | | | | µg/ml | | | | Organan U/ml | | |
| A | dE | 1036 | 827 | 656 | 501 | 405 | 1076 | 220 | 79 | 1070 | 774 | 552 | 423 | 333 |
| A | XU | 101 | 134 | 176 | 226 | 262 | 97 | 344 | 418 | 98 | 145 | 208 | 255 | 292 |
| B | dE | 1492 | 1196 | 974 | 779 | 654 | 1527 | 288 | 117 | 1556 | 1151 | 882 | 708 | 563 |
| B | XU | 101 | 134 | 176 | 225 | 262 | 99 | 399 | 477 | 97 | 141 | 198 | 246 | 293 |
| C | dE | 1028 | 818 | 654 | 518 | 421 | 1040 | 205 | 86 | 1040 | 772 | 587 | 463 | 370 |
| C | XU | 101 | 134 | 177 | 224 | 263 | 100 | 370 | 440 | 100 | 144 | 198 | 245 | 286 |
| D | dE | 981 | 789 | 632 | 509 | 409 | 992 | 218 | 93 | 1006 | 737 | 543 | 437 | 347 |
| D | XU | 101 | 134 | 178 | 222 | 264 | 99 | 362 | 438 | 98 | 147 | 209 | 252 | 294 |
| | XU-mean | 101 | 134 | 176 | 224 | 263 | 99 | 369 | 443 | 98 | 144 | 203 | 249 | 291 |
| | | | | aXa U/ml | | | | µg/ml | | | | Organan U/ml | | |

Figure 6A:
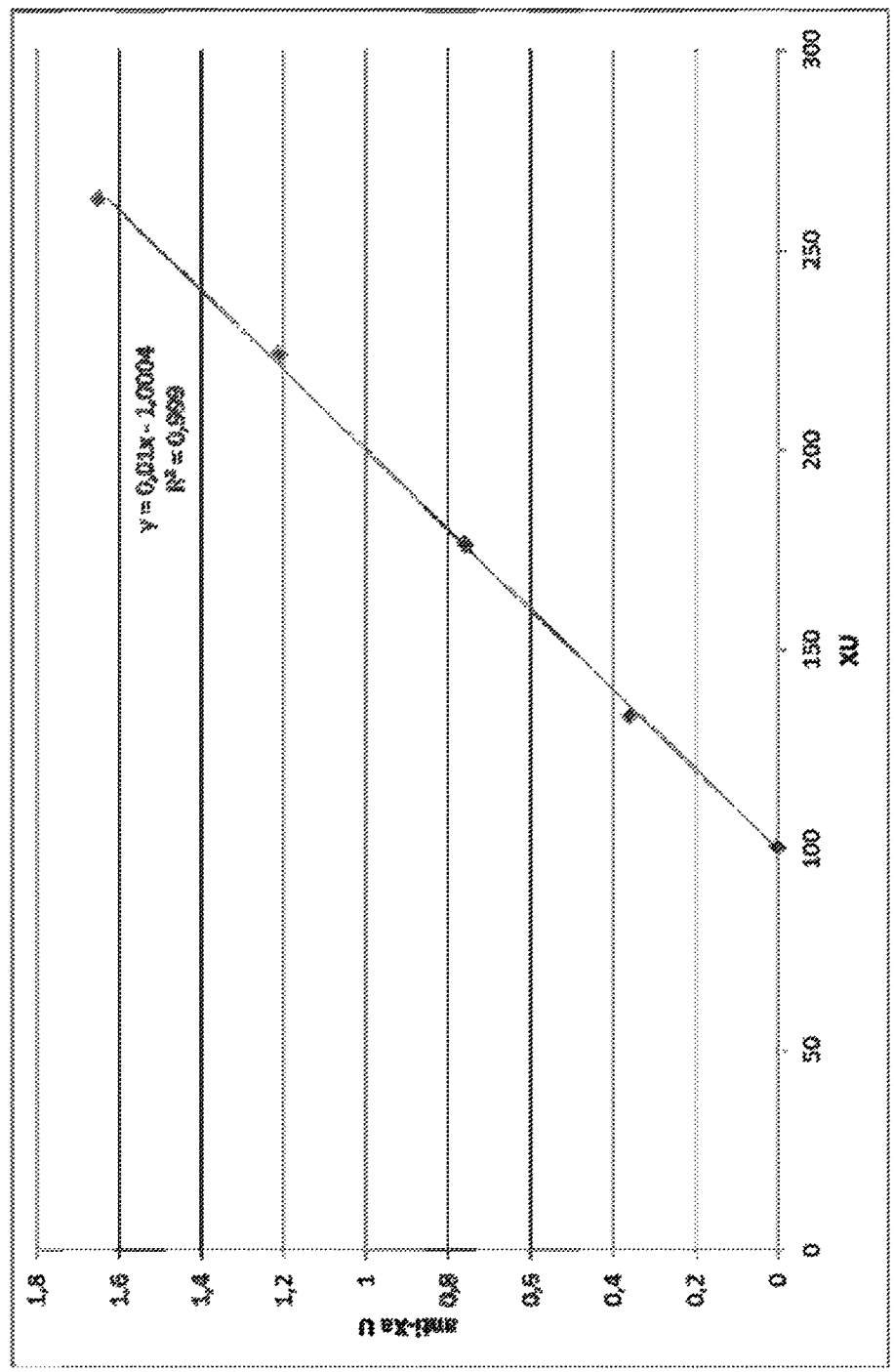
FIG. 6A shows a calibration curve for heparin. activity from the universal calibration units.
Figure 6B:
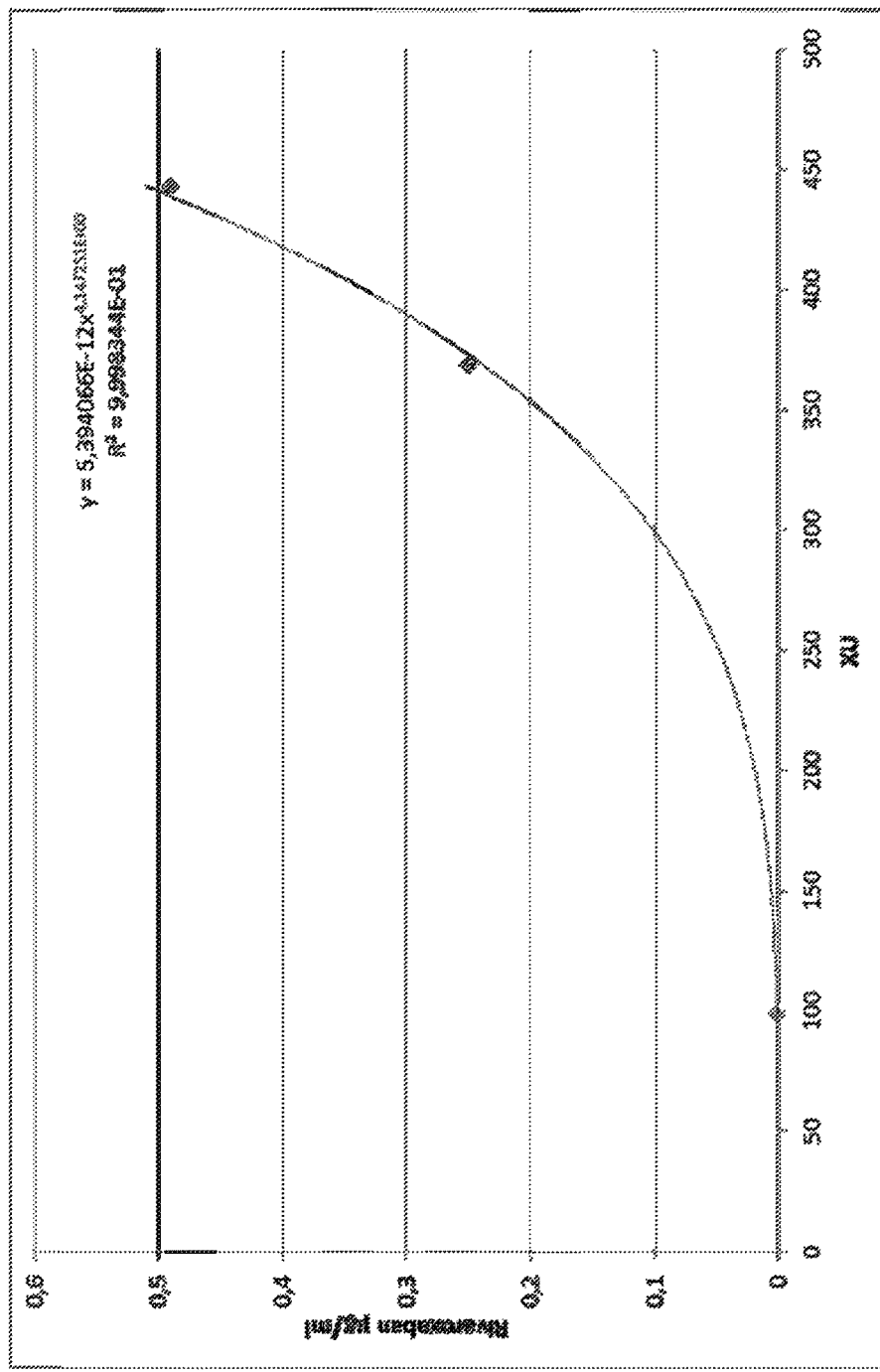
FIG. 6B shows a calibration curve for Rivaroxaban activity from the universal calibration units.
Figure 6C:
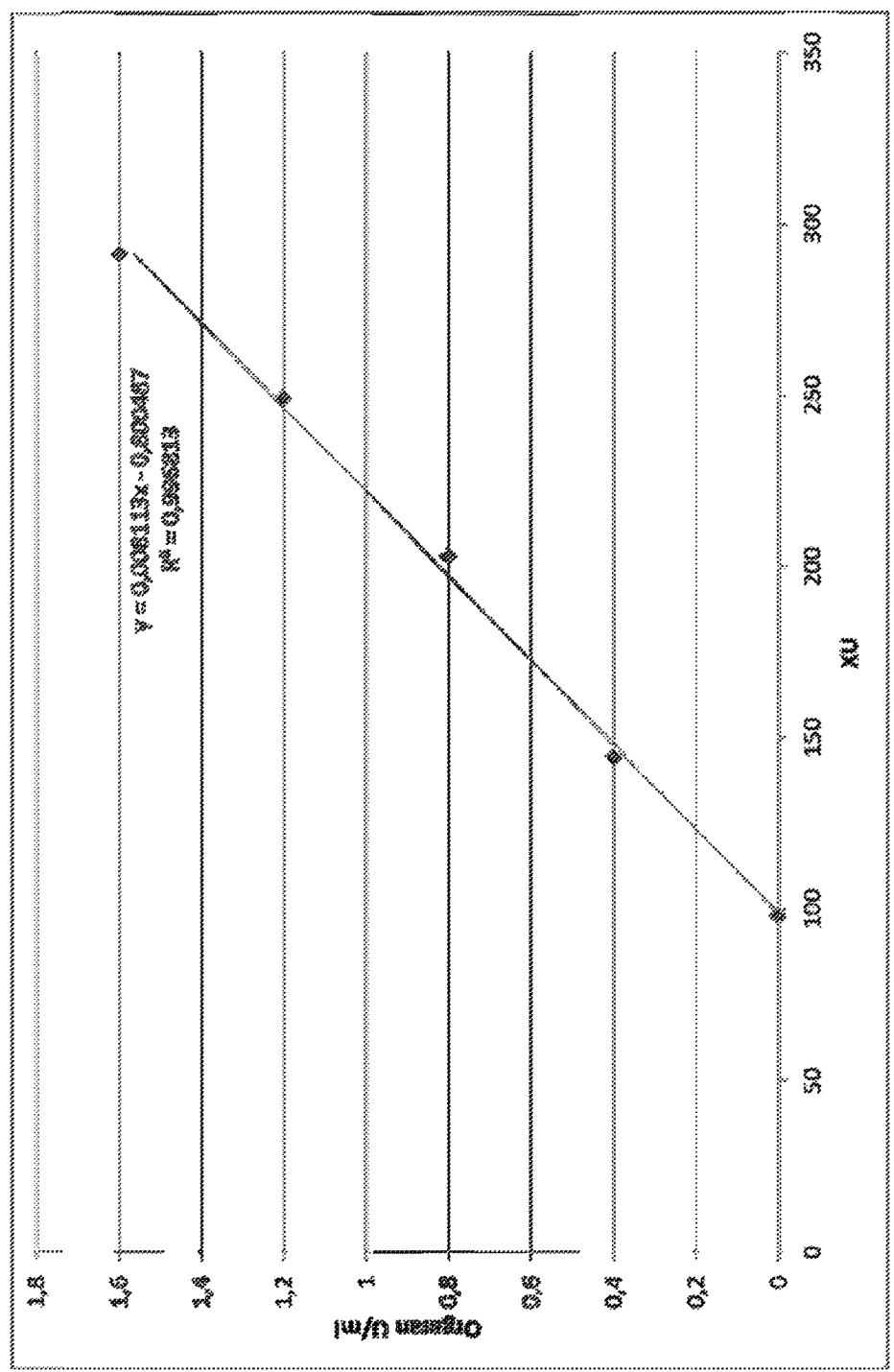
FIG. 6C shows a calibration curve for Organ activity from the universal calibration units.

Based on the mean XU values determined for the calibrators in the four centers, a calibration curve was calculated in order to determine the anticoagulant activity from the XU value; see FIG. 6.

TABLE 10

Regression curves and $R^2$ values for the calibrations to calculate the anticoagulant concentration from the universal calibrated XU values

| Calibration | Regression Curve (x: XU value) | $R^2$ |
|---|---|---|
| Heparin | $0.01x - 1.0004$ | 0.999 |
| Rivaroxaban | $5.394066 * (10^{-12}) * x^{4.147251}$ | 0.999834 |
| Orgaran | $0.008113 * x - 0.800487$ | 0.996813 |

When one uses these regression curves to calculate the anticoagulant concentrations from the XU values, the following results are found for the LMWH samples (and the control sample without anticoagulant activity):

TABLE 11

Anticoagulant concentrations from the XU values for the LMWH samples

| laboratory | day | Control Normal 0 | LMWH Control CI 0.25 | LMWH Control CII 0.48 | LMWH Control C3 0.8 | LMWH Control C4 1.2 | target value |
|---|---|---|---|---|---|---|---|
| A | 1 | −0.05 | 0.24 | 0.51 | 0.80 | 1.28 | |
| A | 1 | −0.04 | 0.22 | 0.55 | 0.91 | 1.32 | |
| A | 2 | 0.01 | 0.31 | 0.58 | 0.89 | 1.33 | |
| A | 2 | −0.03 | 0.29 | 0.50 | 0.83 | 1.26 | |
| A | 3 | −0.04 | 0.25 | 0.52 | 0.86 | 1.28 | |
| A | 3 | −0.03 | 0.25 | 0.51 | 0.85 | 1.26 | |
| B | 1 | −0.01 | 0.26 | 0.47 | 0.79 | 1.44 | |
| B | 1 | −0.01 | 0.18 | 0.48 | 0.81 | 1.30 | |
| B | 2 | 0.00 | 0.18 | 0.53 | 0.88 | 1.37 | |
| B | 2 | 0.04 | 0.23 | 0.51 | 0.80 | 1.31 | |
| B | 3 | 0.01 | 0.18 | 0.48 | 0.81 | 1.23 | |
| B | 3 | 0.02 | 0.23 | 0.48 | 0.83 | 1.29 | |
| C | 1 | −0.03 | 0.26 | 0.84 | 1.05 | 1.22 | |
| C | 1 | −0.03 | 0.20 | 0.77 | 0.82 | 1.32 | |
| C | 2 | −0.02 | 0.23 | 0.47 | 0.83 | 1.27 | |
| C | 2 | −0.02 | 0.27 | 0.51 | 0.86 | 1.31 | |
| C | 3 | −0.02 | 0.24 | 0.51 | 0.88 | 1.26 | |
| C | 3 | −0.02 | 0.24 | 0.52 | 0.80 | 1.24 | |
| D | 1 | −0.04 | 0.27 | 0.51 | 0.84 | 1.29 | |
| D | 1 | −0.03 | 0.28 | 0.51 | 0.84 | 1.32 | |
| D | 2 | −0.04 | 0.23 | 0.49 | 0.86 | 1.34 | |
| D | 2 | −0.03 | 0.23 | 0.50 | 0.84 | 1.30 | |
| D | 3 | −0.05 | 0.23 | 0.47 | 0.83 | 1.29 | |
| D | 3 | −0.04 | 0.27 | 0.50 | 0.84 | 1.32 | |
| | | −0.02 | 0.24 | 0.53 | 0.85 | 1.30 | mean |
| | | | 14.2% | 16.8% | 6.1% | 3.6% | cv |

When one uses these regression curves to calculate the anticoagulant concentrations from the XU values, the following results are found for the Rivaroxaban samples (and the control sample without anticoagulant activity):

TABLE 12A

Anticoagulant concentrations from the XU values for the Rivaroxaban samples

| laboratory | day | Control Normal 0 | Rivar. Control C1 0.09 | Rivar. Control C2 0.3 |
|---|---|---|---|---|
| | | | target value | |
| A | 1 | 0.00 | 0.02 | 0.23 |
| A | 1 | 0.00 | 0.02 | 0.23 |
| A | 2 | 0.00 | 0.02 | 0.24 |
| A | 2 | 0.00 | 0.02 | 0.24 |
| A | 3 | 0.00 | 0.02 | 0.24 |
| A | 3 | 0.00 | 0.02 | 0.22 |
| B | 1 | 0.00 | 0.03 | 0.42 |
| B | 1 | 0.00 | 0.02 | 0.42 |
| B | 2 | 0.00 | 0.02 | 0.43 |
| B | 2 | 0.00 | 0.02 | 0.42 |
| B | 3 | 0.00 | 0.02 | 0.44 |
| B | 3 | 0.00 | 0.02 | 0.42 |
| C | 1 | 0.00 | 0.02 | 0.32 |
| C | 1 | 0.00 | 0.02 | 0.31 |
| C | 2 | 0.00 | 0.02 | 0.32 |
| C | 2 | 0.00 | 0.02 | 0.32 |
| C | 3 | 0.00 | 0.02 | 0.32 |
| C | 3 | 0.00 | 0.02 | 0.30 |
| D | 1 | 0.00 | 0.02 | 0.28 |
| D | 1 | 0.00 | 0.02 | 0.29 |
| D | 2 | 0.00 | 0.03 | 0.29 |
| D | 2 | 0.00 | 0.02 | 0.29 |
| D | 3 | 0.00 | 0.02 | 0.28 |
| D | 3 | 0.00 | 0.02 | 0.28 |
| | | 0.00 | 0.02 | 0.31 | mean |
| | | | 13.8% | 22.5% | CV |

When one uses these regression curves to calculate the anticoagulant concentrations from the XU values, the following results are found for the Orgaran samples (and the control sample without anticoagulant activity):

TABLE 12B

Anticoagulant concentrations from the XU values for the Orgaran samples

| laboratory | day | Control Normal 0 | Orgaran Control C1 0.48 | Orgaran Control C2 1 |
|---|---|---|---|---|
| | | | target value | |
| A | 1 | −0.03 | 0.48 | 1.04 |
| A | 1 | −0.02 | 0.49 | 1.06 |
| A | 2 | 0.02 | 0.51 | 1.14 |
| A | 2 | −0.01 | 0.53 | 1.12 |
| A | 3 | −0.02 | 0.51 | 1.15 |
| A | 3 | −0.01 | 0.50 | 1.12 |
| B | 1 | 0.01 | 0.45 | 1.04 |
| B | 1 | 0.00 | 0.52 | 1.13 |
| B | 2 | 0.01 | 0.47 | 1.08 |
| B | 2 | 0.04 | 0.54 | 1.02 |
| B | 3 | 0.02 | 0.50 | 1.08 |
| B | 3 | 0.02 | 0.46 | 1.08 |
| C | 1 | −0.01 | 0.49 | 1.08 |
| C | 1 | −0.01 | 0.52 | 1.09 |
| C | 2 | −0.01 | 0.54 | 1.06 |
| C | 2 | 0.00 | 0.53 | 1.06 |
| C | 3 | 0.00 | 0.48 | 1.07 |
| C | 3 | −0.01 | 0.47 | 1.02 |
| D | 1 | −0.02 | 0.52 | 1.07 |
| D | 1 | −0.02 | 0.51 | 1.10 |
| D | 2 | −0.02 | 0.50 | 1.11 |
| D | 2 | −0.01 | 0.47 | 1.06 |
| D | 3 | −0.03 | 0.49 | 1.04 |
| D | 3 | −0.02 | 0.49 | 1.05 |
| | | −0.01 | 0.50 | 1.08 | mean |
| | | | 4.9% | 3.3% | cv |

TABLE 13

Comparison of the mean values and CVs for the controls determined via the individual calibrations and via the universal calibration:

| | | target value | Individual calibration | | universal calibration | | |
|---|---|---|---|---|---|---|---|
| Control Normal | Verum | 0 | −0.04 | | −0.02 | | aXa U/ml |
| LMWH Control | CI | 0.25 | 0.25 | 16.3% | 0.24 | 14.2% | aXa U/ml |
| LMWH Control | CII | 0.48 | 0.54 | 16.7% | 0.53 | 16.8% | aXa U/ml |
| LMWH Control | C3 | 0.8 | 0.85 | 6.1% | 0.85 | 6.1% | aXa U/ml |
| LMWH Control | C4 | 1.2 | 1.29 | 3.7% | 1.30 | 3.6% | aXa U/ml |
| Control Normal | Verum | 0 | −0.04 | | 0.00 | | µg Rivaroxaban/ml |
| Rivaroxaban Control | C1 | 0.09 | 0.02 | 14.9% | 0.02 | 13.8% | µg Rivaroxaban/ml |
| Rivaroxaban Control | C2 | 0.3 | 0.30 | 3.5% | 0.31 | 22.5% | µg Rivaroxaban/ml |
| Control Normal | Verum | 0 | 0.00 | | −0.01 | | U Organan/ml |
| Organan Control | C1 | 0.48 | 0.48 | 7.5% | 0.50 | 4.9% | U Organan/ml |
| Organan Control | C2 | 1 | 1.07 | 3.8% | 1.08 | 3.3% | U Organan/ml |

Table 13 shows that the drug concentration data derived from the universal calibration are very similar to the data derived from the individual calibration.

The high CV of the high Rivaroxaban control can be explained by the fact that the XU values were extrapolated for this data point, as the highest calibrator for the XU calibration had only 260 XU, while the high Rivaroxaban control had approx. 400 XU. In a real life situation values above the highest calibrant would be expressed as >260 XU (for example) and or a limited extrapolation would be allowed (e.g., up to values of 110% of the highest calibrant).

In essence, the universal calibration allows to monitor several different anticoagulants directed against Factor Xa using one single calibration curve/one set of controls/one proficiency testing procedure/one SOP, instead of the current state of the art with several calibration curves, several sets of controls, SOPs. Agreement between different days and centers was equally good or better with the universal calibration than using the individual calibrations. It is also possible finally to transform the results of the universal calibration into the actual drug concentrations. In conclusion this method has the potential to significantly simplify the monitoring of Factor Xa inhibitors, reduce costs and improve workflows, while reducing risks and improving the flexibility of the diagnostic method.

New anticoagulants are being constantly introduced into clinical practice. One of the advantages of the inventive method is that new anticoagulants directed against FXa and/or FIIa can be easily tested using the inventive assay without a modification of the test or calibration procedure. On the other hand also for the calibration procedure anticoagulants or other inhibitors of Factor IIa and/or Factor Xa of synthetic or natural origin can be applied.

The invention claimed is:

1. A method for determining an anticoagulant activity elicited by a first anticoagulant in a sample of a subject comprising:
   (a) measuring a first Factor Xa activity in a body fluid test sample of said subject, said body fluid test sample containing a first anticoagulant;
   (b) measuring a second Factor Xa activity in at least one calibrator sample comprising a predefined anticoagulation activity for a second anticoagulant, said second anticoagulant being a chemically different compound than the first anticoagulant; and
   (c) calculating a value of a universal parameter for the anticoagulation activity comprised in the test sample based on the first and the second measured Factor Xa activities by (i) allocating a calibration value of said universal parameter to said second measured Factor Xa activity; (ii) comparing the first Factor Xa activity to the second Factor Xa activity; and (iii) from the result of comparing step (ii), deriving said value of the universal parameter for the first Factor Xa activity from said calibration value.

2. The method of claim 1, wherein said measuring the Factor Xa activity in a sample comprises:
   a) contacting said sample with reagents comprising at least Factor Xa and a Factor Xa substrate under conditions which allow for the enzymatic conversion of the substrate, whereby a physical or chemical property of the substrate is changed in a detectable manner; and
   b) detecting an extent of the change of a physical or chemical property of the Factor Xa substrate; and
   (c) comparing said extent of the change to a reference, whereby the amount of Factor Xa activity in the sample is measured.

3. The method of claim 2, wherein said physical or chemical property is selected from the group consisting of: fluorescence properties, optical properties and electrochemical properties.

4. The method of claim 1, wherein said subject is a mammal.

5. The method of claim 1, wherein said body fluid test sample is a urine sample, a whole blood sample or a blood plasma sample.

6. The method of claim 1, wherein the calibration universal parameter (P) is calculated by the following calculation: P=100+(factor*amount or activity of the anticoagulant used for the calibration), wherein said factor is selected such that a typical therapeutic dose of the anticoagulant provides a universal anticoagulation parameter of 200 arbitrary units.

7. The method of claim 1, wherein said first and/or second anticoagulant is selected from the group consisting of: low molecular weight heparin (LMWH), unfractionated heparin (UFH), Danaparoid, Rivaroxaban, Pentasaccharide, and Apixaban.

8. The method of claim 1, wherein at least step (c) is carried out by a computer implemented algorithm.

9. The method of claim 1, wherein said subject is a human.

* * * * *